(12) United States Patent
Kohn et al.

(10) Patent No.: US 12,030,983 B2
(45) Date of Patent: Jul. 9, 2024

(54) POLYMERIC BIOMATERIALS DERIVED FROM PHENOLIC MONOMERS AND THEIR MEDICAL USES

(71) Applicant: Rutgers, The State University of New Jersey, New Brunswick, NJ (US)

(72) Inventors: Joachim B. Kohn, Piscataway, NJ (US); Durgadas Bolikal, Edison, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 176 days.

(21) Appl. No.: 17/475,914

(22) Filed: Sep. 15, 2021

(65) Prior Publication Data

US 2022/0002478 A1    Jan. 6, 2022

Related U.S. Application Data

(62) Division of application No. 15/208,709, filed on Jul. 13, 2016, now Pat. No. 11,124,603, which is a division of application No. 13/757,752, filed on Feb. 2, 2013, now Pat. No. 9,416,090.

(60) Provisional application No. 61/726,321, filed on Nov. 14, 2012, provisional application No. 61/594,380, filed on Feb. 3, 2012.

(51) Int. Cl.
| | |
|---|---|
| C07C 59/52 | (2006.01) |
| A61K 47/34 | (2017.01) |
| A61L 31/06 | (2006.01) |
| A61L 31/14 | (2006.01) |
| A61L 31/16 | (2006.01) |
| A61L 31/18 | (2006.01) |
| C07C 59/68 | (2006.01) |
| C07C 69/36 | (2006.01) |
| C07C 69/40 | (2006.01) |
| C07C 69/732 | (2006.01) |
| C07C 69/736 | (2006.01) |
| C07C 69/96 | (2006.01) |
| C07C 233/47 | (2006.01) |
| C08G 63/64 | (2006.01) |
| C08G 63/66 | (2006.01) |
| C08G 67/00 | (2006.01) |

(52) U.S. Cl.
CPC ............. *C08G 63/64* (2013.01); *A61K 47/34* (2013.01); *A61L 31/06* (2013.01); *A61L 31/148* (2013.01); *A61L 31/16* (2013.01); *A61L 31/18* (2013.01); *C07C 59/52* (2013.01); *C07C 59/68* (2013.01); *C07C 69/36* (2013.01); *C07C 69/40* (2013.01); *C07C 69/732* (2013.01); *C07C 69/736* (2013.01); *C07C 69/96* (2013.01); *C07C 233/47* (2013.01); *C08G 63/66* (2013.01); *C08G 67/00* (2013.01); *A61L 2300/41* (2013.01); *A61L 2300/412* (2013.01); *A61L 2300/416* (2013.01); *C08G 2230/00* (2013.01)

(58) Field of Classification Search
CPC .... C08G 63/64; C08G 63/66; C08G 2230/00; C07C 59/52
See application file for complete search history.

(56) References Cited

U.S. PATENT DOCUMENTS

| | | |
|---|---|---|
| 2,833,810 A | 5/1958 | Kissman |
| 3,636,956 A | 1/1972 | Schneider |
| 3,663,515 A | 5/1972 | Hostettler et al. |
| 4,043,981 A | 8/1977 | O'Brien |
| 4,162,314 A | 7/1979 | Gottschlich et al. |
| 4,230,817 A | 10/1980 | Charbonneau |
| 4,331,782 A | 5/1982 | Linden |
| 4,476,294 A | 10/1984 | Mark |
| 4,744,365 A | 5/1988 | Kaplan et al. |
| 4,747,956 A | 5/1988 | Kiniwa |
| 4,792,477 A | 12/1988 | Ochiumi |
| 4,822,829 A | 4/1989 | Muller et al. |
| 4,980,449 A | 12/1990 | Kohn et al. |
| 5,003,004 A | 3/1991 | Simms |
| 5,066,772 A | 11/1991 | Tang et al. |
| 5,082,925 A | 1/1992 | Shalaby et al. |
| 5,099,060 A | 3/1992 | Kohn et al. |
| 5,216,115 A | 6/1993 | Kohn et al. |

(Continued)

FOREIGN PATENT DOCUMENTS

| | | |
|---|---|---|
| AU | 2009303332 | 4/2010 |
| CA | 2412161 A1 | 12/2001 |

(Continued)

OTHER PUBLICATIONS

Pettit et al., Heterocycles (2009), 79, 909-916.*

(Continued)

*Primary Examiner* — Shobha Kantamneni
(74) *Attorney, Agent, or Firm* — FOX ROTHSCHILD LLP

(57) ABSTRACT

The present invention provides new classes of phenol compounds, including those derived from tyrosol and analogues, useful as monomers for preparation of biocompatible polymers, and biocompatible polymers prepared from these monomeric phenol compounds, including novel biodegradable and/or bioresorbable polymers. These biocompatible polymers or polymer compositions with enhanced bioresorbabilty and processability are useful in a variety of medical applications, such as in medical devices and controlled-release therapeutic formulations. The invention also provides methods for preparing these monomeric phenol compounds and biocompatible polymers.

10 Claims, No Drawings

(56) References Cited

U.S. PATENT DOCUMENTS

| | | |
|---|---|---|
| 5,219,564 A | 6/1993 | Zalipsky et al. |
| 5,403,347 A | 4/1995 | Roby et al. |
| 5,431,679 A | 7/1995 | Bennett et al. |
| 5,587,507 A | 12/1996 | Kohn et al. |
| 5,660,822 A | 8/1997 | Poiani et al. |
| 5,665,831 A | 9/1997 | Neuenschwander et al. |
| 5,670,602 A | 9/1997 | Kohn et al. |
| 5,698,661 A | 12/1997 | Ferruti et al. |
| 5,702,717 A | 12/1997 | Cha et al. |
| 5,854,383 A | 12/1998 | Emneta et al. |
| 5,916,998 A | 6/1999 | Ferruti et al. |
| 5,952,450 A | 9/1999 | Ishihara et al. |
| 6,120,491 A | 9/2000 | Kohn et al. |
| 6,150,491 A | 11/2000 | Akkara |
| 6,228,969 B1 | 5/2001 | Lee et al. |
| 6,316,585 B1 | 11/2001 | Lele et al. |
| 6,355,754 B1 | 3/2002 | Olson et al. |
| 6,475,477 B1 | 11/2002 | Kohn et al. |
| 6,592,899 B2 | 7/2003 | Fowers et al. |
| 6,602,497 B1 | 8/2003 | Kohn et al. |
| 6,943,214 B2 | 9/2005 | Flexman |
| 7,166,134 B2 | 1/2007 | Datta et al. |
| 7,169,187 B2 | 1/2007 | Datta et al. |
| 7,479,157 B2 | 1/2009 | Weber et al. |
| 8,252,877 B2 | 8/2012 | Hirano et al. |
| 8,252,887 B2 | 8/2012 | Bolikal et al. |
| 8,476,399 B2 | 7/2013 | Bolikal et al. |
| 8,551,511 B2 | 10/2013 | Brandom et al. |
| 2001/0046505 A1 | 11/2001 | Kohn et al. |
| 2003/0068384 A1 | 4/2003 | Brocchini et al. |
| 2004/0082734 A1 | 4/2004 | Hatton et al. |
| 2005/0106119 A1 | 5/2005 | Brandom et al. |
| 2006/0024266 A1 | 2/2006 | Brandom et al. |
| 2006/0034769 A1 | 2/2006 | Kohn et al. |
| 2006/0034891 A1 | 2/2006 | Lawin et al. |
| 2006/0036316 A1 | 2/2006 | Zeltinger et al. |
| 2006/0178477 A1 | 8/2006 | Neuenschwander |
| 2007/0117959 A1 | 5/2007 | Shastri et al. |
| 2007/0135355 A1 | 6/2007 | Bezwada |
| 2007/0183996 A1 | 8/2007 | Okombi et al. |
| 2007/0190151 A1 | 8/2007 | Chai et al. |
| 2007/0231365 A1 | 10/2007 | Wang et al. |
| 2007/0282435 A1 | 12/2007 | Wang et al. |
| 2008/0063685 A1 | 3/2008 | Wang et al. |
| 2008/0112999 A1 | 5/2008 | Baluca |
| 2008/0146504 A1 | 6/2008 | Bonnin |
| 2008/0152690 A1 | 6/2008 | Kohn et al. |
| 2008/0187567 A1 | 8/2008 | Kohn et al. |
| 2008/0221295 A1 | 9/2008 | Ishikawa et al. |
| 2008/0243049 A1 | 10/2008 | Hardy |
| 2008/0243228 A1 | 10/2008 | Wang et al. |
| 2008/0269874 A1 | 10/2008 | Wang et al. |
| 2009/0004243 A1 | 1/2009 | Pacetti et al. |
| 2009/0011055 A1 | 1/2009 | Lawrence et al. |
| 2009/0035350 A1 | 2/2009 | Stankus et al. |
| 2009/0088835 A1 | 4/2009 | Wang |
| 2009/0288753 A1 | 11/2009 | Calhoun et al. |
| 2010/0228343 A1 | 9/2010 | Brandom et al. |
| 2010/0234555 A1 | 9/2010 | Bolikal et al. |
| 2013/0085238 A1 | 4/2013 | Bolikal et al. |
| 2013/0203713 A1 | 8/2013 | Kohn et al. |
| 2014/0046018 A1 | 2/2014 | O'Shea et al. |
| 2015/0045451 A1 | 2/2015 | Bolikal et al. |
| 2016/0376401 A1 | 12/2016 | Kohn et al. |

FOREIGN PATENT DOCUMENTS

| | | |
|---|---|---|
| CA | 2412718 A1 | 1/2002 |
| CA | 2486104 A1 | 5/2004 |
| CA | 2737764 A1 | 4/2010 |
| CN | 102492429 A | 6/2012 |
| DE | 3523977 | 1/1986 |
| JP | H0618946 A | 1/1994 |
| JP | 107292084 A | 11/1995 |
| JP | H07295221 A | 11/1995 |
| JP | H11513985 A | 11/1999 |
| JP | 2004-513971 | 5/2004 |
| JP | 2007-506791 | 3/2007 |
| JP | 2007131622 A | 5/2007 |
| JP | 2008506019 A | 2/2008 |
| JP | 2008-509722 | 4/2008 |
| JP | 2008-510034 | 4/2008 |
| JP | 2009503187 A | 1/2009 |
| WO | 1989/001005 A1 | 2/1989 |
| WO | 91/06569 A1 | 5/1991 |
| WO | 9715287 A1 | 5/1997 |
| WO | 1997/019996 | 6/1997 |
| WO | 1998/036013 A1 | 8/1998 |
| WO | 1999/024391 | 5/1999 |
| WO | 2005030268 A1 | 4/2005 |
| WO | 2006/022754 A2 | 3/2006 |
| WO | 2006/060235 A2 | 6/2006 |
| WO | 2007/018544 A2 | 2/2007 |
| WO | 2007047244 A2 | 4/2007 |
| WO | 2007/050583 A2 | 5/2007 |
| WO | 2007/056134 | 5/2007 |
| WO | 2007/143698 | 12/2007 |
| WO | 2008/082738 A2 | 7/2008 |
| WO | 2008105652 A1 | 9/2008 |
| WO | 2010/033640 | 3/2010 |
| WO | 2010/042917 | 4/2010 |
| WO | 2010042917 A1 | 4/2010 |
| WO | 2010042918 A1 | 4/2010 |
| WO | 2015/126666 A1 | 8/2015 |
| WO | 2016028292 A1 | 2/2016 |

OTHER PUBLICATIONS

Vijayasankar et al., Comptes Rendus Chimie, 2011, 14(12), 1109-1116.*

5-(4-Carboxy-1,4-Dioxobutoxy)Tryptophan, Compound w2ith 5-Hydroxy-6-Methylpyridine-3,4-Dimethanol (1:1), Chemical Book, Retrieved from the Internet:<URL: http://www.chemicalbook.com/ChemicalProductProperty_CN_CB1896543.htm>.

Beaulieu, et al: "Non-Nucleoside Inhibitors of the Hepatitis C Virus NS5B Polymerase: Discovery of Benzimidazole 5-Carboxylic Amid Derivatives with Low-Nanomolar Potency", Bioorganic & Medicinal Chemistry Letters, 2004, vol. 14, pp. 967-971.

Berse, et al: "The Preparation of Succinamido Peptides", Journal of Organic Chemistry, Published 1962, vol. 27, pp. 3489-3495.

Caracciolo, P.C. et al., Effect of the hard segment chemistry and structure on the thermal and mechanical properties of novel biomedical segmented poly(esterurethanes), J. Mater Sci: Mater Med (2009) 20:145-155.

Cascales, et al: "Tiratricol Neutralizes Bacterial Endotoxins and Reduces Lipopolysaccharide-Induced TNF-x Production in the Cell", Chem Biol Drug Des, 2008, vol. 72, pp. 320-328.

Database Caplus, Chemical Abstracts Service, Feb. 1, 1995 (3 pages) XP-002762086.

Database WPI, Week 199602, Thomson Scientific, 1996 (2 pages), XP-002762099.

Covello, et al: "Synthesis and Properties of 2-Hydroxy-And 2-Acetoxy-5-Iodobenzoic Acid Polyesters of Short-Chain Aliphatic Polyalcohols", Oct. 1, 1968, La Ricerca Scientifica, vol. 38, No. 10, pp. 933-936.

Dobrzynski et al. Structure-Property Relationships of Copolymers Obtained by Ring-Opening Polymerization of Glycolide and e-Caprolactone. Part 1. Synthesis and Characterization. Biomacromolecules 6(1): 483-488. 2005.

Du, et al, "Synthesis, Characterization and Biodegradation of Biodegradeable-Cum-Photoactive Liquid-Crystalline Copolyesters Derived from Ferulic Acid", Polymer, Elsevier Science Publishers B.V., GB, vol. 48, No. 19, Sep. 4, 2007, pp. 5541-5547.

Fuso et al, "Poly[(w-hydroxyalkyl)thio-a-cyanocinnamates]. Linear Polyesters with NLO-Phores in the Main Chain", Macromolecules vol. 24, pp. 1710-1713 (1991).

Georgeoussis, et al: "Molecular Mobility in Halogen-Containing Side-Chain Liquid-Crystalline Polymers Studied by Dielectric Spectroscopy", Polymer International, 2000, vol. 49, pp. 975-980.

Green and Wuts, "Protective Groups in Organic Synthesis" 3rd Ed. John Wiley & Sons, New York, NY, 1999 (Abstract only).

(56) References Cited

OTHER PUBLICATIONS

Imasaka, K. et al., "New Biodegradable Polymers of L-Lactic Acid and Aromatic Hydroxy Acids and Their Applications in Drug Delivery Systems", International Journal of Pharmaceutics, Elsevier BV, NL, vol. 81, No. 1, Mar. 15, 1992, pp. 31-38.

Imasaka, et al: "Synthesis and In Vitro Degradations of Low-Molecular-Weight Copolyesters Composed of L-lactic Acid and Aromatic Hydroxy Acids", Makromolekular Chemmie, 1990, vol. 191, pp. 2007-2082.

Ji et al: "Polyester-based Ink Platform with Tunable Bioactivity for 3D Print of Tissue Engineering Scaffolds", Biomaterials Science, 2018, 00, 1-3.

Jin, X et al., "Synthesis, Characterization, and In Vitro Degradation of a Novel Thermotropic Ternary Copolyester Based on P-Hydroxybenzoic Acid, Glycolic Acid, and P-Hydroxycinnamic Acid", Macromolecules, American Chemical Society, US, vol. 28, No. 14, Jul. 3, 1995, pp. 4785-4794.

Kakemi, et al: "Studies on the Pharmaceutical Potentiation of Drugs", Chemical & Pharmaceutical Bulletin, Dec. 1967, vol. 15, No. 12, pp. 1819-1827.

Kalgutkar, et al: "Design, Synthesis, and Biochemcial Evaluation of N-Substituted Maleimides as Inhibitors of Prostaglandin Endoperoxide Synthases", J. Med. Chem., 1996, vol. 39, pp. 1692-1703.

Kaneko et al., "Environmentally degradable, high-performance thermoplastics from phenolic phytomonomers", Nature Materials, vol. 5, pp. 966-970 (2006).

Kaneko, "High-Performance Functional Ecopolymers Based on Flora and Fauna", Chemical Record vol. 7(4), pp. 210-219 (2007).

Krawczyk, et al: "A Study on Horseradish Peroxidase-Mediated Coupling of Phenolesters, Directed To Synthesis of Lythraceae Alkaloids", Bulletin of the Polish Academy of Sciences, 1986, vol. 34, No. 3-4, pp. 115-122.

Latham, K et al., "Development of Support Matrices for Affinity Chromatography of Thyroid Hormone Receptors," The J. of Biological Chem, Dec. 10, 1981, vol. 256, pp. 12088-12093.

Laurencin, et al. "Poly(anhydride) administration in high doses in vivo: studies of biocompatibility and toxicology", J. Biomed. Mat. Res.; 1463-1481, 1990 (Abstract only).

Liskamp, et al., "Synthesis of Alkyne-Bridged Cyclic Tripeptides toward Constrained Mimics of Vancomycin", J. Org. Chem. 2006, 71, 5, 1817-1824 (Abstract only).

Majeska, et al: "Effects of Plate Preparation on Results in Microbial Mutation Assays", Environmental and Molecular Mutagenesis, 1992, vol. 19, pp. 244-252.

Matsusaki, M et al., "Synthesis and Characterization of Novel Biodegradeable Polymers Composed of Hydroxycinnamic Acid and D,L-Lactic Acid", Journal of Applied Polymer Science, vol. 82, No. 10, Sep. 19, 2001, pp. 2357-2364.

Mikroyannidis, "Synthesis, properties and crosslinking of unsaturated cyano-substituted homo- and copolyesters prepared from 1-hydroxy-4-(2-cyano-2-carboxyvinyl)benzene", Polymer vol. 36(6), pp. 1287-1293 (1995).

Milewska et al: "Synthesis of Symmetric and Asymmetric Diamides of Citric Acid and Amino Acids", Amino Acids, 1994, vol. 7, pp. 89-96.

Mligiliche et al., "Poly lactic acid-caprolactone copolymer tube with a denatured skeletal muscle segment inside as a guide for peripheral nerve regeneration: A morphological and electrophysiological evaluation of the regenerated nerves," Anatomical Science International, vol. 78, No. 3, Sep. 2003, pp. 156-161. (Abstract).

Moody, et al: "Aerothionin and Homoaerothionin: Two Tetrabromo Spirocyclohexedi-enylisoxazoles from Verongia Sponges", Journal of the Chemical Society, Perkin Transactions: Organic and Bio-Organic Chemistry, 1972, No. 1, pp. 18-24.

Mosher et al., "Polypeptides from r-Phenylalanine Mustard", J. Med. Chem. vol 7(5), pp. 650-652 (1964).

Nagata, M. et al., "Biodegradable Elastic Photocured Polyesters Based on Adipic Acid, 4-Hydroxcinnamic Acid and Poly(Epsilon-Caprolactone) Diols", Polymer, Elsevier Science Publishers B.V., GB, vol. 45, No. 1, Jan. 1, 2004, pp. 87-93.

Nathan, et al., "Copolymers of Lysine and Polyethylene Glycol: A New Family" Bio. Cong. Chem., (1993) vol. 4, pp. 54-62.

Nathan, et al., "Hydrogels Based on Water-Soluble Poly(ether urethanes) Derived from L-Lysine and Poly(ethylene glycol)" Macromol., (1992) vol. 25, pp. 4476-4484.

Padmaja, et al.: "Enzymatically Degradable Prodrugs: A Novel Methodology for Drug Linkage", 2002, Journal of Applied Polymer Sciences, vol. 85, Issue 10, pp. 2108-2118.

Perez, P. et al., "Bioresorbable and Nonresorbable Macroporous Thermosensitive Hydrogels Prepared by Cryopolymerization. Role of the Cross-Linking Agent," Biomacromolecules 2008, vol. 9, pp. 66-74.

Plage et al.: "Therman Degradation and Mass Spectrometric Fragmention Processes of Polyesters Studies by Time-/Temperature-Resolved Pyrolysis-Field Ionization Mass Spectrometry", Macromolecules, 1990, vol. 23, pp. 2642-2648.

Plate, et al., "Comb-like polymers. Structure and properties." J. Polymer Sci., Macromol. Rev. vol. 8, pp. 117-253 (1974) (Abstract only).

Polycarprolactone diol, 2011 obtained from the Sigma-Aldrich website: (http://www.sigmaaldrich.com/catalog/ProductDetail.do?D7=0&N5=SEARCH_CONCAT_PNO%7CBRAND_KEY&N4=189421%7CALDRICH&N25=0&QS=ON&F=SPEC).

Ross, et al.: "Carbon Suboxide and Proteins"; Journal of Biological Chemistry, Published 1941, vol. 37, pp. 105-111.

Sarkar, D., et al., Structure-Property Relationship of L-Tyrosine-Based Polyurethanes for Biomaterial Applications, Journal of Applied Polymer Science, vol. 108, 23435-2355 (2008).

Schmaljohann et al., Conversion dependence of the structural units and the degree of branching of a hyperbranched polyester based on 4,4-bis-(4'-hydroxyphenyl)pentanoic acid determined by NMR spectroscopy, Acta Polym. vol. 50, pp. 196-204 (1999).

Shiotani, et al: "Studies on Diazabenzobicyclo[3.3.1]noname System. VIII.1) Synthesis of 8,9-Dimethoxy-11-benzoyl-1,2,5,6-tetrahydro-2,6-imino-3-benzazocin-4(3-H)-one", Chem. Pharm. Bull, 1968, vol. 16, No. 2, pp. 239-245.

Sommerfeld, et al.: "Structural Investigations of Polycarbonates whose Mechanical and Erosion Behavior Can Be Controlled by Their Isomer Sequence", Macromolecules, Nov. 12, 2020, vol. 53, pp. 9878-9889.

Sousa, A., et al., "Selective Protein Adsorption on a Phase-Separated Solvent-Cast Polymer Blend", Langmuir, 22, 2006, pp. 6286-6292.

Tang, S et al., "Synthesis and Characterization of Water-Soluble and Photostable L-DOPA Dendrimers," Organic Letters, 2006, vol. 8, No. 20, pp. 4421-4424.

Tangpasuthadol, V., et al., "Thermal properties and physical ageing behaviour of tyrosine-derived polycarbonates", Biomaterials, 1996, vol. 17, No. 4., pp. 463-468.

Ten Brink et all: "Synthesis of Alkyne-Bridged Cyclic Tripeptides Toward Constrained Mimics of Vancomycin", 2006, Journal of Organic Chemistry, vol. 71, No. 5, pp. 1817-1824.

Teng et al., "Synthesis and characterization of poly(L-lactic acid)-poly(e-caprolactone) multiblock copolymers by melt polycondensation," Journal of Polymer Science Part A: Polymer Chemistry. 42: pp. 5045-5053, 2004. (Abstract).

Trisuwan, et al., "Anthraquinone Cyclopentanone, and Napthoquinone Derivatives from the Sea Fan-Derived Fungi *Fusarium* spp. PSU-F14 and PSU-F135", J. of Natural Products, vol. 73, No. 9, Sep. 2010, pp. 1507-1511.

Trisuwan, et al., "Supporting Information—Anthraquinone Cyclopentanone, and Napthoquinone Derivatives from the Sea Fan-Derived Fungi *Fusarium* spp. PSU-F14 and PSU-F135", J. of Natural Products, Sep. 24, 2010, pp. 1-12.

Valivety, et al: "Application of Enzymes to the Synthesis of Amino Acid-Based Bola and Gemini Surfactants", Journal of Surfactants and Detergents, Apr. 1998, vol. 1, No. 2, pp. 177-185.

Wermann, K. et al., Photoreactive Polyanhydrides Containing Cinnamic Acid Units in the Main Chain, Macromolecular Reports, A31(Suppls. 6&7, 1279-1283 (1994).

Yang, et al., "Phenolic constituents from the rhizomes of Gastrodia elata", Database CA (online) Chemical Abstracts Service, Columbus, Oh; Yang et al., "Phenolic constituents from the rhizomes of

(56) References Cited

OTHER PUBLICATIONS

Gastrodia elata" XP002711180, retrieved frm STN Database accession No. 2007:23882 (abstract); Yang et al., "Phenolic constituents from the rhizomes of Gastrodia elata", Natural Product Research, 21(2) pp. 180-186 (abstract).

Zhang, et al.: "Synthesis and Biological Activities of QuinazolineDerivatives with Ortho-Phenol_Quaternary Ammonium Salt Groups", Bioorganic & Medicinal Chemistry, 2007, vol. 15, Issue 22, pp. 6920-6926.

Kongkiat, et al., "Anthraquinone Cyclopentanone, and Napthoquinone Derivatives from the Sea Fan-Derived Fungi *Fusarium* spp. PSU-F14 and PSU-F135", J. of Natural Products, vol. 73, No. 9, Sep. 2010, pp. 1507-1511.

Kongkiat, et al., "Supporting Information—Anthraquinone Cyclopentanone, and Napthoquinone Derivatives from the Sea Fan-Derived Fungi *Fusarium* spp. PSU-F14 and PSU-F135", J. of Natural Products, Sep. 24, 2010, pp. 1-12.

\* cited by examiner

POLYMERIC BIOMATERIALS DERIVED FROM PHENOLIC MONOMERS AND THEIR MEDICAL USES

CROSS-REFERENCE TO RELATED APPLICATIONS

This application is a Divisional of U.S. Nonprovisional application Ser. No. 15/208,709, filed on Jul. 13, 2016, which is a Divisional of U.S. Non-provisional application Ser. No. 13/757,752, filed on Feb. 2, 2013, now U.S. Pat. No. 9,416,090, issued on Aug. 16, 2016, which claims priority under 35 U.S.C. § 119(e) to U.S. Provisional Patent Application Ser. No. 61/594,380, filed on Feb. 3, 2012, and Ser. No. 61/726,321, filed on Nov. 14, 2012. The disclosures of the foregoing applications are hereby incorporated by reference in their entireties.

FIELD OF THE INVENTION

The present invention relates to new classes of monomeric phenol compounds useful for preparation of biocompatible polymers and biocompatible polymers prepared therefrom, including novel biodegradable and/or bioresorbable polymers. These polymers, while not limited thereto, may be adapted for radio-opacity and are useful for medical device applications and controlled release therapeutic formulations.

BACKGROUND OF THE INVENTION

The rapidly evolving field of bioengineering has created a demand for a diverse library of different types of polymers offering a wide variety of choice of physical, mechanical, chemical and physiological properties. It is desirable that libraries of many different materials be available so that the specific polymer properties can be optimally matched with the requirements of the specific applications under development.

Examples of polymers suitable for various bioengineering applications include those described in U.S. Pat. Nos. 5,099,060; 5,665,831; 5,916,998 and 6,475,477, along with the polymers described in U.S. Patent Publication Nos. 2006/0024266 and 2006/0034769. There are numerous applications in which it is considered desirable for an implanted medical device to maintain its integrity and performance characteristics for extended periods of time, even under demanding mechanical conditions such as repeated mechanical flexure. Although many types of bioresorbable and/or biodegradable polymers are known, in most of these polymers diphenolic monomers are prepared by linking two suitably protected tyrosine molecules or tyrosine analogs via an amide linkage. These amide linkages do not degrade hydrolytically under physiological conditions and therefore the monomers which have low solubility in water, dissolve very slowly. Further, due to hydrogen bonding of amide hydrogen the melt viscosity of the polymers derived from these monomers are very high, which makes thermal processing more difficult. In addition, bioresorbtion and/or biodegradation tend to alter mechanical properties in unpredictable ways that are not necessarily linearly related to each other.

Thus, there is a need for biocompatible polymers having desirable bioresorbabilty and biodegradability as well as good processability under thermal conditions. There remains a need for nontoxic polyarylates having a moderate rate of bioerosion, suitable for use as tissue-compatible materials for biomedical uses.

SUMMARY OF THE INVENTION

The present invention addresses the foregoing need by providing new monomers useful for the preparation of the desired biocompatible polymers and various types of such polymers useful for making the implantable medical devices.

The present invention broadly relates to diphenolic monomers and bioerodible polymers synthesized using such monomers. In various embodiments, the diphenolic monomers are derived from tyrosine and/or tyrosine analogs. In particular, in one preferred aspect the present invention relates to bioerodible polycarbonates and polyarylates derived from the naturally occurring 4-(2-hydroxylethyl) phenol (or "tyrosol") and phosgene and/or biocompatible dicarboxylic acids.

In one aspect the present invention provides biocompatible polymers comprising a repeating structural unit of Formula (I):

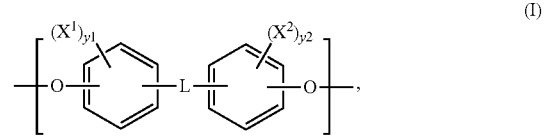

wherein L is —$R^1$-A-$R^2$—;

A is a linking group selected from:

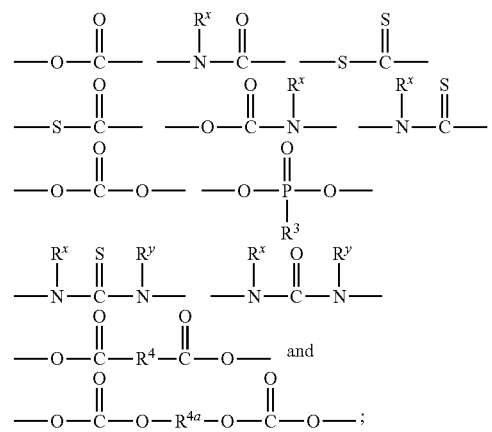

$X^1$ and $X^2$, at each occurrence, are independently halogen (F, Cl, Br, or I);

$y^1$ and $y^2$ have values independently selected from 0, 1, 2, 3 and 4;

$R^1$ and $R^2$ are each independently selected from straight-chain or branched, saturated or unsaturated, substituted or unsubstituted, alkylene, alkenylene, alkylarylenoxy, heteroalkylene and heteroalkenylene containing up to 12 carbon atoms, said alkylene, alkenylene, heteroalkylene and heteroalkenylene optionally containing a pendant Z group and optionally comprising one, two or three heteroatoms independently selected from O, $NR^z$ and S;

$R^3$ is selected from the group consisting of hydrogen, $C_1$-$C_{30}$ alkyl, $C_1$-$C_{30}$ heteroalkyl, $C_2$-$C_{30}$ alkenyl, $C_2$-$C_{30}$ alkynyl, $C_2$-$C_{30}$ heteroalkenyl, and $C_2$-$C_{30}$ heteroalkynyl;

$R^4$ is selected from the group consisting of a bond, $C_1$-$C_{30}$ alkyl, $C_2$-$C_{30}$ alkenyl, $C_2$-$C_{30}$ alkynyl, $C_1$-$C_{30}$ heteroalkyl, $C_2$-$C_{30}$ heteroalkenyl, $C_2$-$C_{30}$ heteroalkynyl, $C_6$-$C_{30}$ aryl, $C_7$-$C_{30}$ alkylaryl, $C_5$-$C_{30}$ alkenylaryl, $C_5$-$C_{30}$ alkynylaryl, and $C_2$-$C_{30}$ heteroaryl;

$R^{4a}$ is selected from the group consisting of $C_1$-$C_{30}$ alkyl, $C_2$-$C_{30}$ alkenyl, $C_2$-$C_{30}$ alkynyl, $C_1$-$C_{30}$ heteroalkyl, $C_2$-$C_{30}$ heteroalkenyl, $C_2$-$C_{30}$ heteroalkynyl, $C_6$-$C_{30}$ aryl, $C_7$-$C_{30}$ alkylaryl, $C_5$-$C_{30}$ alkenylaryl, $C_5$-$C_{30}$ alkynylaryl, and $C_2$-$C_{30}$ heteroaryl;

Z is $-N(R^x)C(=O)R^5$, $-N(R^x)COOR^6$, $-COOR^7$ or $-CONR^xR^y$, wherein $R^5$, $R^6$, $R^7$, $R^x$ and $R^y$, at each occurrence, are independently selected from hydrogen, alkyl, aryl, alkylaryl, arylalkyl, heteroalkyl, and heteroalkylaryl group containing up to 30 carbon atoms, wherein the heteroalkyl group contains from 1 to 10 heteroatoms independently selected from O, N and S and the heteroalkylaryl group contains from 1 to 3 heteroatoms independently selected from O, N and S.

In an embodiment, the heteroatom in the heteroalkyl and/or heteroalkylaryl group is N in the form of a $NR^z$ group, wherein $R^z$ is selected from the group consisting of H, $C_1$-$C_{30}$ alkyl, and arylalkyl containing up to 30 carbon atoms.

In various embodiments, $R^x$ in the definition of A and L in formula (I) is an alkyl group, e.g., a branched or unbranched $C_1$-$C_6$ alkyl. For example, in an embodiment, $R^x$ in formula (I) is a methyl. In various embodiments, $R^1$ and $R^2$ are each independently $-(CH_2)_m-$ and $-(CH_2)_n-$, respectively, where n and m are each independently integers in the range of one to 12. For example, in an embodiment, $R^1$ is $-(CH_2)_m-$ and $R^2$ is $-(CH_2)_n-$, and n and m are each independently 1 or 2. In some embodiments, $R^1$ is $-O-(CH_2)_m-$ or $-O-C_6H_4-(CH_2)_m-$, where the $-C_6H_4-$ is optionally substituted phenyl (e.g., optionally substituted with 1 or 2 halogens such as Br and/or I) and n and m are each independently integers in the range of one to 12 (e.g., 1 or 2). Similarly, in some embodiments, $R^2$ is independently $-(CH_2)_n-O-$ or $-(CH_2)_n-C_6H_4-O-$, where the $-C_6H_4-$ is independently optionally substituted phenyl (e.g., optionally substituted with 1 or 2 halogens such as Br and/or I) and n and m are each independently integers in the range of one to 12 (e.g., 1 or 2).

$X^1$ and $X^2$ in formula (I) can be independently selected to be any halogen atom. In an embodiment, $X^1$ and $X^2$ in formula (I) are each I. In an embodiment, $X^1$ and $X^2$ in formula (I) are each Br. In some embodiments, the $X^1$ and $X^2$ groups on the polymer comprising a recurring unit of formula (I) are iodine.

Those skilled in the art will appreciate that the presence of oxygen atoms on both ends of the repeating structural unit of Formula (I) does not imply end-to-end linkage of such repeating units to form oxygen-oxygen bonds. Instead, it will be appreciated that the polymer containing the repeating structural unit of Formula (I) can also contain one or more other repeating units. For example, in another aspect the present invention provides polymers containing the repeating structural unit of Formula (I) and further containing recurring units represented by $A^1$. Examples of such polymers include polycarbonates, polyarylates, polyiminocarbonates, polyphosphazenes and polyphosphoesters, comprising the repeating structure of Formula (II):

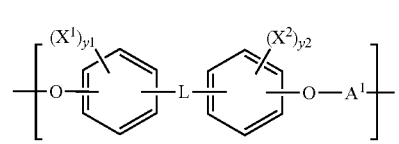

wherein L, $X^1$, $X^2$, $y^1$, and $y^2$ are defined as above; and $A^1$ is a linking group selected from:

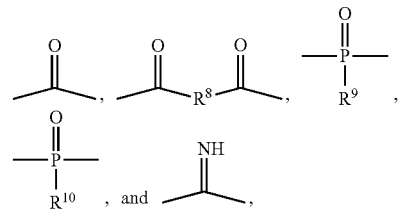

wherein $R^8$ is selected from a bond, $C_1$-$C_{30}$ alkyl, $C_2$-$C_{30}$ alkenyl, $C_2$-$C_{30}$ alkynyl; $C_1$-$C_{30}$ heteroalkyl, $C_2$-$C_{30}$ heteroalkenyl, $C_2$-$C_{30}$ heteroalkynyl, $C_7$-$C_{30}$ heteroalkylaryl, $C_5$-$C_{30}$ heteroalkenylaryl, $C_5$-$C_{30}$ heteroalkynylaryl, $C_7$-$C_{30}$ alkylaryl, $C_5$-$C_{30}$ alkenylaryl, $C_5$-$C_{30}$ alkynylaryl, and $C_2$-$C_{30}$ heteroaryl; and $R^9$ and $R^{10}$ are each independently selected from H, $C_1$-$C_{30}$ alkyl, $C_1$-$C_{30}$ heteroalkyl, $C_2$-$C_{30}$ alkenyl, $C_2$-$C_{30}$ alkynyl, $C_2$-$C_{30}$ heteroalkenyl, and $C_2$-$C_{30}$ heteroalkynyl.

In another aspect the present invention provides diphenolic monomers having the following generic structure of Formula (III):

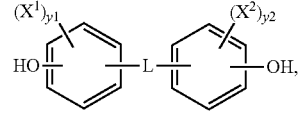

wherein L, $X^1$ and $X^2$, $y^1$ and $y^2$ are defined as above. Such monomers are useful for making polymers that comprise repeating structural units of Formula (I) as described in greater detail below.

In one particular aspect this invention provides diphenolic monomers derived from hydroxyalkylphenol having a generic structure of Formula (IV):

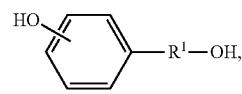

wherein $R^1$ is defined as above. $R^1$ is preferably a $C_1$-$C_{12}$ alkylene, e.g., a $C_1$-$C_4$ alkylene. More preferably $R^1$ is ethylene ($-CH_2-CH_2-$). Most preferably, the hydroxyalkylphenol is 4-(2-hydroxyethyl)phenol or 2-(4-hydroxyphenyl)ethanol (or "tyrosol") having the following structure:

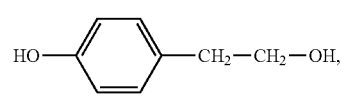

which is a natural product present in olive oil and white wine and has been shown to have both antioxidant and cardioprotective properties. The phenyl ring of tyrosol can be halogenated, and those skilled in the art will understand that teachings herein regarding tyrosol can be applied to such halogenated forms as well. Tyrosol can be converted into a diphenolic monomer, e.g., a diphenolic ester, in several ways. It can be esterified with desaminotyrosine (DAT) or N-protected tyrosine to form a diphenolic monomer with an ester linkage. It can also be esterified with 0.5 mole equivalents of dicarboxylic acids to provide a family of diphenolic diester monomers that can be introduced into polymers to control chain flexibility, as needed. Those skilled in the art will appreciate that use of ring halogenated compounds (e.g., halogenated tyrosol, halogenated DAT, etc.) results in the corresponding halogenated polymers.

Thus, in one preferred embodiment the present invention provides a new class of diphenolic monomers of the Formula (V):

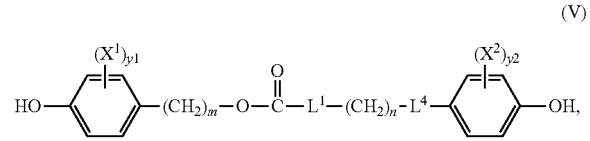

(V)

wherein $L^1$ is a bond, oxygen (—O—) or —$R^4$—C(O)—O—, $L^4$ is a bond, oxygen (—O—) or optionally substituted phenoxy (—$C_6H_4$—O—), m and n are each independently integers in the range of one to 12, and $X^1$, $X^2$, y1, y2 and $R^4$ are as defined above. In an embodiment, $R^4$ is selected from saturated and unsaturated, substituted and unsubstituted, alkylene and alkylarylene groups containing up to 18 carbon atoms. In another embodiment, m and n are each independently 1 or 2. For example, an embodiment provides a monomer of the Formula (Va):

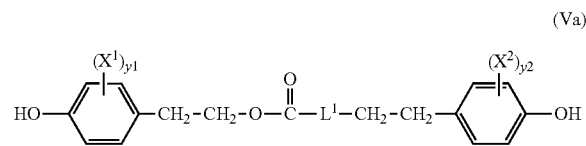

(Va)

wherein $L^1$, $X^1$, $X^2$, y1, and y2 are as defined above.

Such monomers can be made from optionally halogenated tyrosol as described in greater detail below.

In another preferred embodiment the present invention provides a class of diphenolic monomers of the Formula (VI):

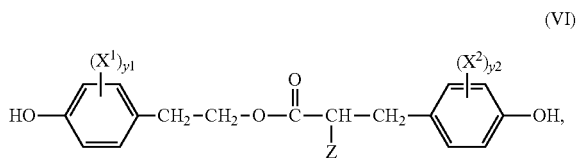

(VI)

wherein $X^1$, $X^2$, y1, y2 and Z are as defined above. For example, in an embodiment, Z is —N($R^x$)C(=O)$R^5$ or —N($R^x$)COO$R^6$, where $R^5$, $R^6$, and $R^x$ are as defined above. Such monomers can be made from optionally halogenated 2-(4-hydroxyphenyl)ethanol as described in greater detail below.

The diphenolic monomers described herein, e.g., of the Formulae (III), (V) and (VI), can be polymerized using phosgene to form polycarbonates or with dicarboxylic acids to obtain polyarylates. The diphenolic monomers can also be copolymerized with other diphenols (such as desaminotyrosyl tyrosine ethyl ester) and other dihydroxyl compounds such as poly(ethylene glycol), polycaprolactone-diol, poly(trimethylene carbonate), polylactide and/or polyglycolide. The polymers can be made radio-opaque by introducing halogen, in particular iodine and/or bromine atoms, on the phenyl rings. Other optionally halogenated phenolic alcohols can be used in place of tyrosol, and other optionally halogenated aromatic carboxylic acids can be used in place of DAT.

Preferred biocompatible polymers that can be made using the monomers described herein include those comprising a recurring structural unit of the following Formula (VII), (VIIa), (VIII), and/or (VIIIa):

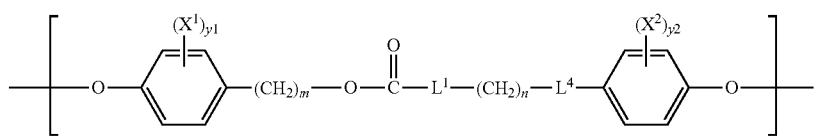

(VII)

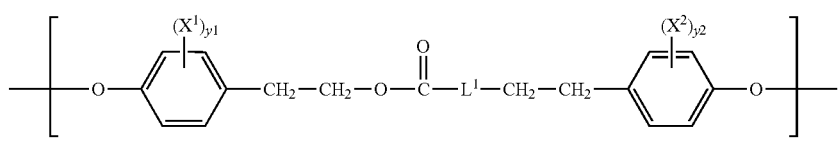

(VIIa)

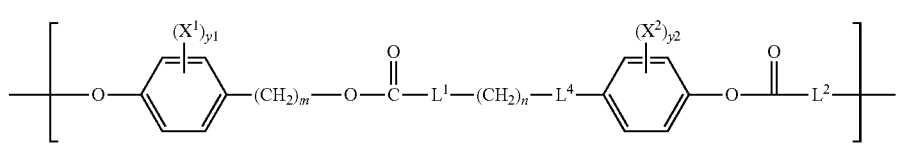

(VIII)

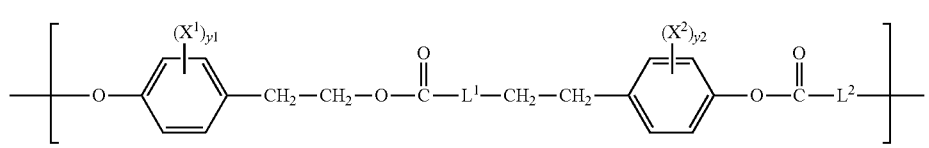

wherein $L^2$ is a bond or —$R^8$—C(O)—, and m, n, $L^1$, $L^4$, X, $X^2$, y1, y2 and $R^8$ are defined above. In an embodiment, $R^4$ (in the definition of L) and $R^8$ (in the definition of $L^2$) are each independently selected from saturated and unsaturated, substituted and unsubstituted, alkylene and alkylarylene groups containing up to 18 carbon atoms.

Those skilled in the art will appreciate that, depending on the manner and extent to which the aromatic rings are substituted, the polymers described herein can have various configurations. For example, the following Formulae (VIIIb), (VIIIc), (VIIId), and (VIIIe) illustrate various embodiments of a polymer containing recurring units of Formula (VIII) in which $X^1$ and $X^2$ are Br, y1 and y2 are 1, $L^1$ is O and $L^2$ is a bond:

In another aspect, the present invention provides a medical device comprising a biocompatible polymer described herein. In a preferred embodiment, the medical device is a stent.

Also provided herein is a method for making a polymer that comprises a recurring unit of formula (I). In an embodiment, the method of making the polymer comprises attaching an N-substituent during the synthesis of a corresponding monomer. In an embodiment, the method of making the polymer comprises attaching an N-substituent during polymerization of a corresponding monomer. In an embodiment, the method of making the polymer comprises attaching an N-substituent after polymerization of a corresponding

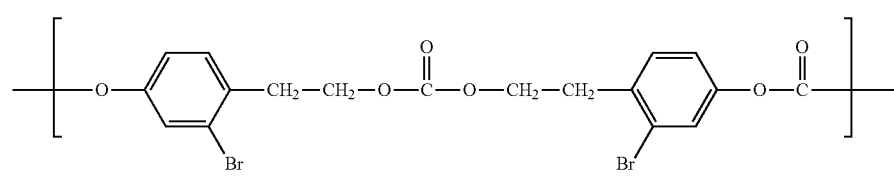

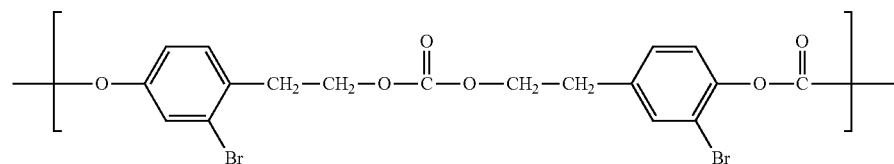

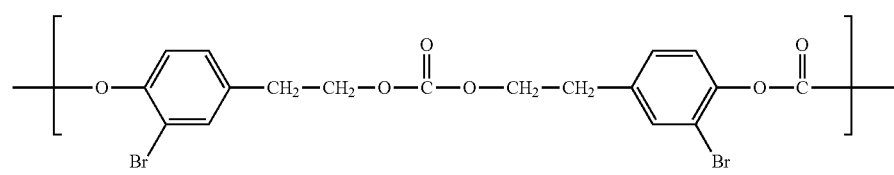

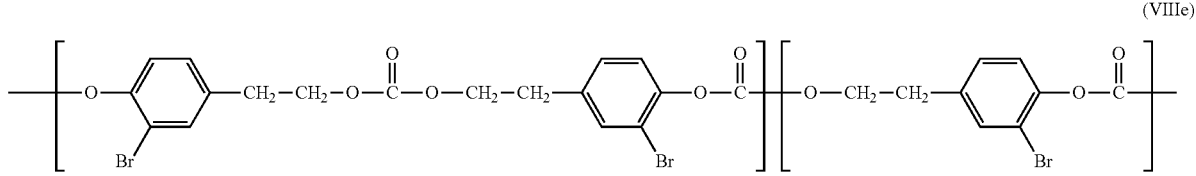

It is surprisingly discovered that replacing the amide bond with an ester bond can provide a solution to one or both of the resorbability and processability issues mentioned above. First, the ester bond cleaves hydrolytically to produce water-soluble fragments, thus increasing the resorption rate of the polymer. Second, reducing the level of amide hydrogens tends to lower the melt viscosity of the polymer, thus allowing facile thermal fabrication.

In another aspect, the present invention provides a polymer composition comprising a biocompatible polymer described herein.

monomer. Methods of making a polymer comprising a recurring unit of the formula (I) are further discussed in detail below.

These and other embodiments are described in greater detail below.

DETAILED DESCRIPTION OF THE INVENTION

To meet the need of versatile moldable biodegradable and biocompatible polymers made using relatively nontoxic monomeric starting materials, the present application describes a variety of such monomers and polymers prepared from these monomers.

Therefore, in one aspect the present invention provides a polymer comprising a repeating structural unit of Formula (I) in which L is —$R^1$-A-$R^2$— and in which A is any one of the various linking groups set forth above. Those skilled in the art will appreciate that for any of these "A" groups illustrated above, the depicted group is not limited to the formula shown, when it is asymmetrical between the left and the right, but it also encompasses the corresponding mirror image of the formula, when such an arrangement would not violate known chemical bonding principles. For example, the group denoted as

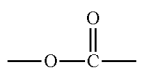

also encompasses

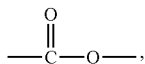

and the group denoted as

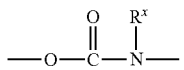

also encompasses

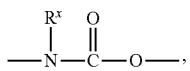

when these groups would fit into any of the Formulae described above. A similar principle applies to any of the formulae, or a portion thereof, described herein, when similar asymmetry exists. All the formulae drawn out in this application merely serve as illustrations, and are not intended to be limiting.

In another aspect the present invention provides polymers, such as polycarbonates, polyarylates, polyiminocarbonates, polyphosphazenes and polyphosphoesters, comprising the repeating structure of Formula (II) as set forth above in which L is —$R^1$-A-$R^2$— and in which A and $A^1$ can be any combination of any of the various linking groups defined above for A and $A^1$, respectively. The same principle applies to other portions or substituents of the various monomers and repeating structural units described herein. Thus, this disclosure is intended to describe all such combinations.

Another aspect of the present invention provides diphenolic monomers that are capable of being polymerized to form polycarbonates or polyarylates. The monomers provided by this aspect of the present invention are diphenolic compounds having the structure of Formula III set forth above, and in some embodiments can be considered to be tyrosine or tyrosol derivatives.

In another aspect the present invention provides a polymer comprising the repeating structure of Formula (Ia):

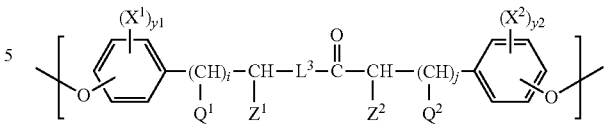

wherein:
i and j are each independently zero (0) or an integer selected from 1 through 6;
$X^1$, $X^2$, $y^1$, and $y^2$ are defined as above;
$Q^1$ and $Q^2$, at each occurrence, are each independently hydrogen, halogen, or alternatively two adjacent $Q^1$'s or $Q^2$'s form a bond;
$L^3$ is oxygen (O) or —$NR^x$—, wherein $R^x$ is as defined above;
$Z^1$ is hydrogen, —C(O)$OR^7$ or —C(O)$NR^xR^y$, wherein $R^7$, $R^x$ and $R^y$ are as defined above;
$Z^2$ is hydrogen, —N($R^x$)C(=O)$R^5$ or —N($R^x$)COO$R^6$, wherein $R^5$, $R^6$, and $R^x$ are as defined above.

In another aspect the present invention provides a polymer comprising the repeating structure of Formula (IIa):

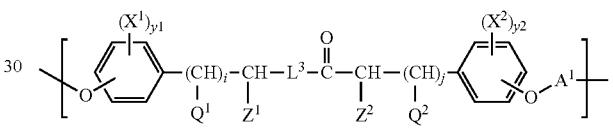

wherein i, j, $y^1$, $y^2$, $X^1$, $X^2$, $Q^1$, $Q^2$, $Z^1$, $Z^2$, $L^3$ and $A^1$ is as defined above.

In another aspect the present invention provides a polymer comprising the repeating structure of Formula (Ib):

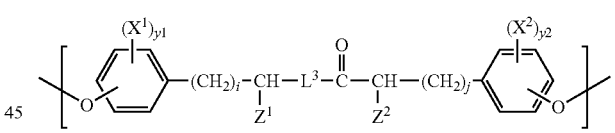

wherein i, j, $y^1$, $y^2$, $X^1$, $X^2$, $Z^1$, $Z^2$, and $L^3$ are as defined above.

In another aspect the present invention provides a polymer comprising the repeating structure of Formula (IIb):

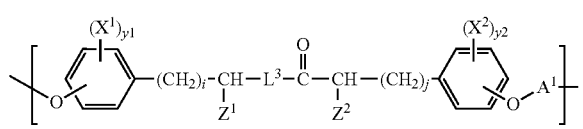

wherein i, j, $y^1$, $y^2$, $X^1$, $X^2$, $Z^1$, $Z^2$, $L^3$ and $A^1$ are as defined above.

In an embodiment, the present invention incorporates the discovery that useful polyarylates can be prepared from tyrosol-derived diphenol compounds. For example, in an embodiment, the present invention provides a polymer comprising the repeating structure of Formula (IIc):

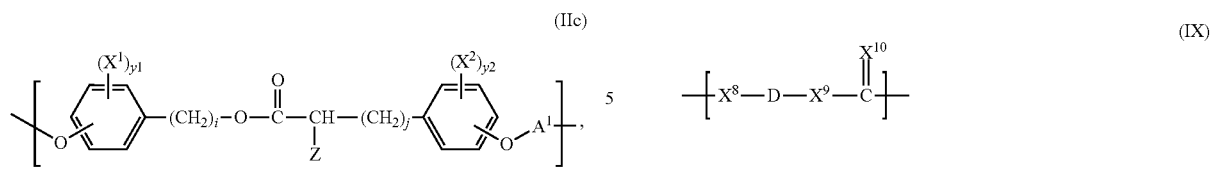
(IIc)

wherein i, j, $y^1$, $y^2$, $X^1$, $X^2$, Z, and $A^1$ are as defined above. In an embodiment, Z is hydrogen, $-N(R^x)C(=O)R^5$, or $-N(R^x)COOR^6$, wherein $R^5$, $R^6$, and $R^x$ are as defined above.

In another aspect, the present invention provides a polymer comprising the repeating structure of Formula (Ic):

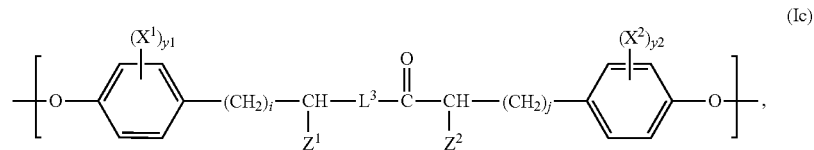
(Ic)

wherein i, j, $y^1$, $y^2$, $X^1$, $X^2$, $Z^1$, $Z^2$, and $L^3$ are as defined above.

In another aspect, the present invention provides a polymer comprising a recurring unit of structure (IId):

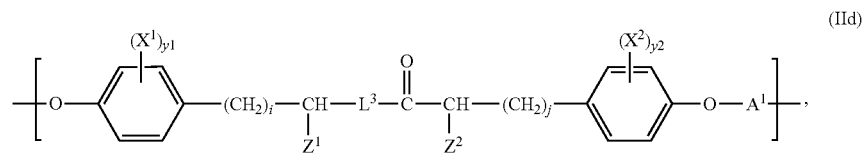
(IId)

wherein i, j, y, $y^2$, $X^1$, $X^2$, $Z^1$, $Z^2$, $L^3$ and $A^1$ are as defined above.

In various embodiments of this aspect, $A^1$ is any one of the $A^1$ linking groups set forth above; i is 1 or 2; and/or j is 1 or 2.

In another aspect, the present invention provides a polymer comprising a recurring unit of structure (Id):

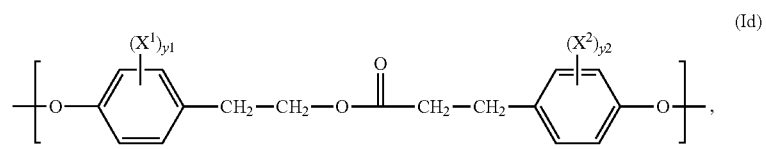
(Id)

wherein $X^1$, $X^2$, $y^1$, and $y^2$ are defined as above. In an embodiment, $X^1$ and $X^2$ are independently Br or I; and $y^1$ and $y^2$ are independently 0, 1, or 2.

In another aspect, the present invention provides a biocompatible polymer composition, comprising at least a first polymer component and a second polymer component. In an embodiment, the first polymer component comprises a number (n) of first recurring units of formula (Ic) as set forth above, and the second polymer component comprises recurring units having a formula selected from the group consisting of the formula (IX), the formula (X), the formula (XI), and the formula (XII):

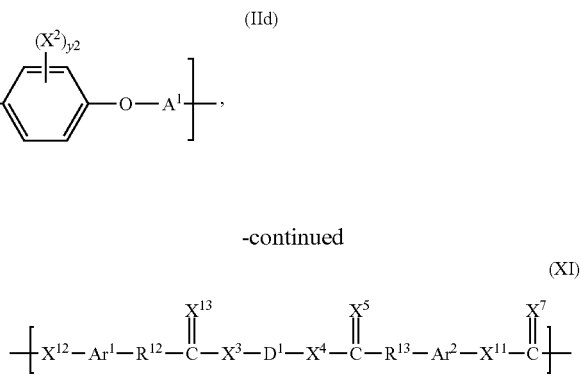

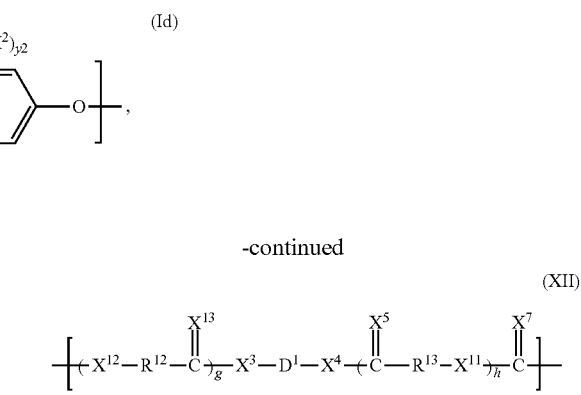

wherein $X^3$, $X^4$, $X^5$, $X^7$, $X^8$, $X^9$, $X^{10}$, $X^{11}$, $X^{12}$ and $X^{13}$ are independently selected from the group consisting of O, S and $NR^{11}$, where $R^{11}$ is selected from hydrogen and an alkyl group containing from one to 30 carbon atoms;

Ar¹ and Ar² are phenyl rings optionally substituted with from one to four substituents independently selected from the group consisting of a halogen, a halomethyl, a halomethoxy, a methyl, a methoxy, a thiomethyl, a nitro, a sulfoxide, and a sulfonyl;

R¹² and R¹³ contain from one to ten carbon atoms each and are independently selected from the group consisting of an optionally substituted alkylene, an optionally substituted heteroalkylene, an optionally substituted alkenylene, and an optionally substituted heteroalkenylene;

g and h in formula (XII) are each independently integers in the range of about 1 to about 500; and D and D¹ contain up to 24 carbon atoms and are independently selected from the group consisting of an optionally substituted alkylene, an optionally substituted heteroalkylene, an optionally substituted alkenylene and an optionally substituted heteroalkenylene;

or D, X⁸ and X⁹ in formula (IX) are selected so that HX⁸-D-X⁹H defines a hydroxyl endcapped macromer, a mercapto endcapped macromer or an amino endcapped macromer;

or D¹, X³ and X⁴ in formula (XI) are selected so that HX³-D¹-X⁴H defines a hydroxyl endcapped macromer, a mercapto endcapped macromer or an amino endcapped macromer.

In a preferred embodiment of this aspect, the first polymer component comprises a recurring unit of formula (Id) as set forth above.

In other aspects, the present invention provides copolymers that comprise any two or more of the recurring units described herein. For example, in an embodiment, the polymer comprises two or more recurring units selected from the group of recurring units represented by Formula (I), Formula (Ia), Formula (Ib), Formula (Ic), Formula (Id), Formula (II), Formula (IIb), Formula (IIc), Formula (IId), Formula (VII), Formula (VIII), Formula (VIIIa), Formula (VIIIb), Formula (VIIIc), Formula (VIIId), Formula (VIIIe), Formula (IX), Formula (X), Formula (XI), Formula (XII), Formula (XIII), Formula (XIV), Formula (XV), Formula (XVIa), Formula (XVIb), and Formula (XVIc). In another embodiment, the polymer comprises at least two recurring units resulting from the polymerization of any two or more monomers described herein. For example, in an embodiment, the polymer comprises two or more recurring units resulting from copolymerization of two or more monomers selected from the group of monomers represented by Formula (III), Formula (IV) (tyrosol), Formula (V), Formula (VI), tyrosine ethyl ester (TE), mono-iodinated TE (ITE), di-iodinated TE (I₂TE), desaminotyrosine (DAT), mono-iodinated DAT (IDAT), di-iodinated DAT (I₂DAT), desaminotyrosyl tyrosine ethyl ester (DTE), mono-iodinated DTE (IDTE), di-iodinated DTE (I₂DTE), N-desaminotyrosyl mono-iodinated tyrosine ethyl ester (DITE), and N-desaminotyrosyl di-iodinated tyrosine ethyl ester (DI₂TE).

For example, an embodiment provides a polymer that contains recurring units of the Formula (II) in which L is —R¹-A-R²—, R¹ and R² are —(CH₂)₂—, A is

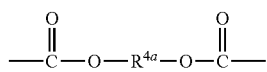

and A¹ is

as represented by the following Formula (XIII):

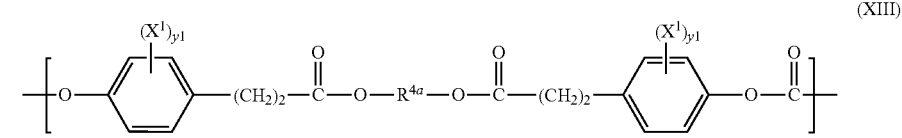

In an embodiment, the polymer is a copolymer that contains tyrosol recurring units and recurring units of the Formula (II). An example of a copolymer containing such recurring units is represented by the following Formulae (XIIIa) and XIIIb):

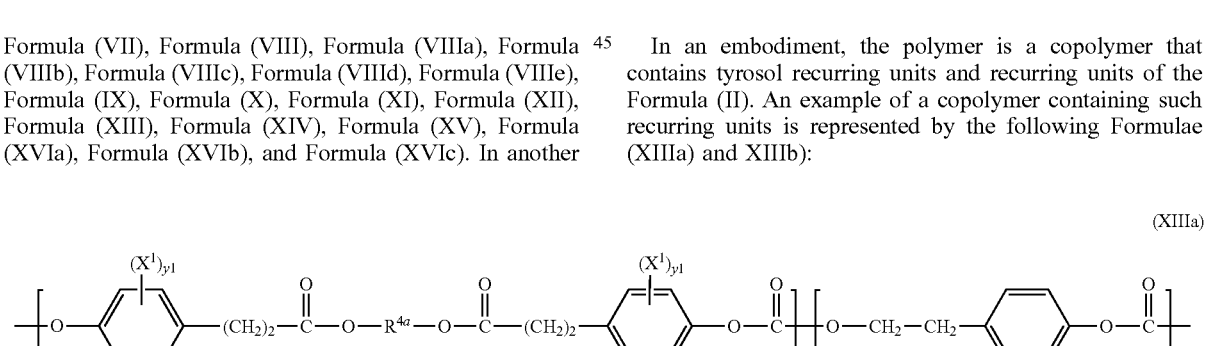

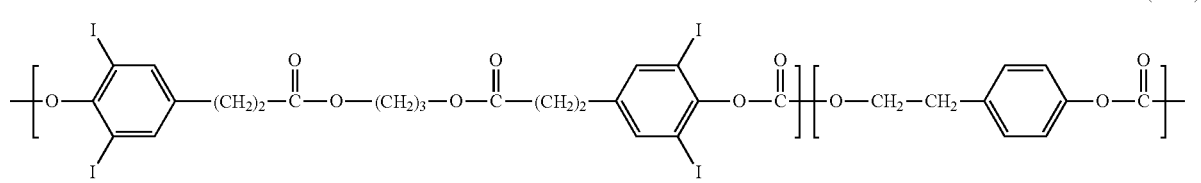

In an embodiment, the polymer is characterized by Formula:

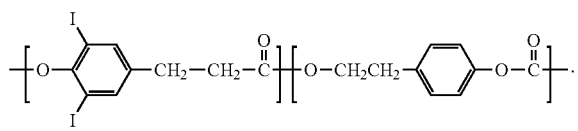

In another embodiment, the polymer is characterized by Formula:

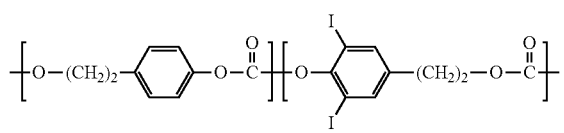

Those skilled in the art will appreciate that polymers containing the recurring units of Formulae (XIIIa) and (XIIIb) contain a tyrosol recurring unit and a recurring unit of Formula (II) in which L is —$R^1$-A-$R^2$—, $R^1$ and $R^2$ are —$(CH_2)_2$—, A is

and $A^1$ is

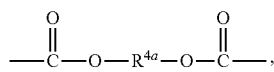

Those skilled in the art will also appreciate that, for Formula (XIIIb), $X^1$ and $X^2$ are I, y1 and y2 are 2, and $R^{4a}$ is —$(CH_2)_3$—.

Those skilled in the art will also appreciate that the two recurring units in Formulae (XIIIa) and (XIIIb) can appear in a polymer molecule in a variety of possible arrangements. Using Formula (XIIIb) to illustrate, without intending to be bound by theory, depending on polymerization reaction conditions, the PrD-di $I_2$DAT carbonate and tyrosol carbonate recurring units can be arranged in any order. That is, two adjacent units could include "PrD-di$I_2$DAT-PrD-di$I_2$DAT", "PrD-di$I_2$DAT-tyrosol", or "tyrosol-tyrosol". Given the unsymmetrical structure of tyrosol, it can be connected with a PrD-di$I_2$DAT unit using either its "head" (i.e., "phenoxy" moiety) or "tail" (i.e., the "ethylenoxy" moiety). Any two adjacent units formed from tyrosol itself can be in any of the "head-head", "head-tail" and "tail-tail" arrangements. In particular, when the polymerization reaction is conducted in a manner as described in Example 12, where triphosgene is added to a mixture of PrD-di$I_2$DAT and tyrosol, the poly (PrD-di$I_2$DAT-co-tyrosol carbonate) product is composed of mainly polymer molecules having randomly-ordered PrD-di$I_2$DAT and tyrosol recurring units connected through carbonate (—OC(O)O—) linkers. Unless specifically described otherwise, any recurring units designated as -[A]-[B]—, such as Formulae (XIIIa) and (XIIIb) above and Formulae (XVIa), (XVIb) and (XVIc) below, encompass all possible such arrangements as hereby explained.

In other aspects of the invention, the polymer comprises a backbone which is not naturally occurring. Alternatively and/or additionally, the polymer may comprise a backbone comprising at least one amino acid derivative.

A polymer comprising a recurring unit as described herein can be copolymerized with any number of other recurring units. In an embodiment, a polymer comprising a recurring unit of any one or more of Formula (I), Formula (Ia), Formula (Ib), Formula (Ic), Formula (Id), Formula (II), Formula (IIb), Formula (IIc), Formula (IId), Formula (VII), Formula (VIII), Formula (VIIIa), Formula (VIIIb), Formula (VIIIc), Formula (VIIId), Formula (VIIIe), Formula (IX), Formula (X), Formula (XI), Formula (XII), and/or Formula (XIII), further comprises a recurring unit of the formula (XIV):

 (XIV)

wherein:
B in formula (XIV) is —O—$((CHR)_p$—$O)_q$—;
each R is independently H or $C_1$ to $C_3$ alkyl;
p and q are each independently an integer in the range of from about 1 to about 100; and
$A^1$ is as defined above, independently from any other $A^1$.

In preferred embodiments, Formula (XIV) includes polyethylene glycol (PEG) recurring units (R=H and p=2), polyproplyene glycol (PPO) recurring units (p=2, and two adjacent R's=H and $CH_3$, respectively) and/or poly(trimethylene carbonate) (PTMC) recurring units (R=H, q=1, p=3 and $A^1 =$ 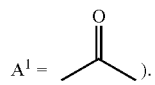 ).

Various polycarbonates and polyarylates of the present invention employ diphenol compounds derived from tyrosol as a starting material. Examples of tyrosol-derived diphenol monomer compounds suitable for the formation of polycarbonates or polyarylates have the structure depicted by Formula (III) defined as above.

The polymer is expected to hydrolyze to release the original diphenol and diacid, thus forming nontoxic degradation products, provided that the monomeric starting materials are nontoxic. The toxicological concerns associated with polyarylates are met by using diphenols derived from tyrosol and phosgene or dicarboxylic acids that are either metabolites or highly biocompatible compounds.

Therefore, another aspect of the present invention provides molded articles prepared from the polymers of the present invention.

Based on the foregoing, in certain embodiments of the biocompatible polymers described herein, $A^1$ is a carbonyl group having a structure of

wherein the carbonyl group is derived from a phosgene starting material. This method is essentially the conventional method for polymerizing diols into polycarbonates. Suitable processes, associated catalysts and solvents are known in the art and are taught in, for example, Schnell, Chemistry and Physics of Polycarbonates, (Interscience, New York 1964), the teachings of which are incorporated herein by reference. Other methods adaptable for use to prepare the poly-carbonate and other phosgene-derived polymers of the present invention are disclosed in U.S. Pat. Nos. 6,120,491 and 6,475,477 the disclosures of which are incorporated by reference.

In another embodiment of the polymers described herein, $A^1$ is a group having the structure:

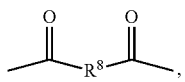

which is a recurring unit derived from a carboxylic acid starting material or monomer. When the monomer used to form the polymer is a diphenol, the diphenol can be reacted with an aliphatic or aromatic dicarboxylic acid in the carbodiimide mediated process disclosed by U.S. Pat. No. 5,216,115 using 4-(dimethylamino) pyridinium-p-toluene sulfonate (DPTS) as a catalyst. The disclosure of U.S. Pat. No. 5,216,115 is incorporated by reference, and particularly for the purpose of describing such polymerization methods. This process forms polymers with —O—C(=O)—$R^8$—C(=O)—O— linkages. $R^8$ may be selected so that the dicarboxylic acids employed as starting materials are either important naturally-occurring metabolites or highly biocompatible compounds. Aliphatic dicarboxylic acid starting materials therefore include the intermediate dicarboxylic acids of the cellular respiration pathway known as the Krebs Cycle. The dicarboxylic acids include α-ketoglutaric acid, succinic acid, fumaric acid and oxaloacetic acid ($R^8$ may be —$CH_2$—$CH_2$—C(=O)—, —$CH_2$—$CH_2$—, —CH=CH— and —$CH_2$—C(=O)—, respectively).

Yet another naturally occurring aliphatic dicarboxylic acid is adipic acid ($R^8$ is —$(CH_2)_4$—), found in beet juice. Still another biocompatible aliphatic dicarboxylic acid is sebacic acid ($R^8$ is —$(CH_2)_8$—), which has been studied extensively and has been found to be nontoxic as part of the clinical evaluation of poly(bis(p-carboxyphenoxy)propane-co-sebacic acid anhydride) by Laurencin et al., J. Biomed. Mater. Res., 24, 1463-81 (1990).

Other biocompatible aliphatic dicarboxylic acids include oxalic acid ($R^8$ is a bond), malonic acid ($R^8$ is —$CH_2$—), glutaric acid ($R^8$ is —$(CH_2)_3$—), pimelic acid ($R^8$ is —$(CH_2)_5$—), suberic acid ($R^8$ is —$(CH_2)_6$—) and azelaic acid ($R^8$ is —$(CH_2)_7$—). $R^8$ can thus represent —$(CH_2)_n$—, where n is between 0 and 8, inclusive. Among the suitable aromatic dicarboxylic acids are terephthalic acid, isophthalic acid and bis(p-carboxy-phenoxy) alkanes such as bis(p-carboxy-phenoxy) propane.

Preferred polymers comprise a recurring unit as described herein, e.g., a recurring unit selected from the group of recurring units represented by Formula (I), Formula (Ia), Formula (Ib), Formula (Ic), Formula (Id), Formula (II), Formula (IIb), Formula (IIc), Formula (IId), Formula (VII), Formula (VIII), Formula (VIIIa), Formula (VIIIb), Formula (VIIIc), Formula (VIIId), Formula (VIIIe), Formula (IX), Formula (X), Formula (XI), Formula (XII), Formula (XIII), Formula (XIV), Formula (XV), Formula (XVIa), Formula (XVIb), and Formula (XVIc). Preferred polymers can contain combinations of derivatives of structural units selected from dicarboxylic acids, halogenated (e.g., iodinated or brominated) derivatives of desaminotyrosyl-tyrosine and poly(alkylene glycols), which exhibit desirable physicomechanical and physicochemical properties that are consistent with their use in fabrication of medical devices, including stents. For example, the stents described in accordance with preferred embodiments of the present invention: (a) are sufficiently radiopaque to be visible by conventional X-ray fluoroscopy; (b) are of sufficient strength to support medically relevant levels of radial compression within an artery or surrounding tissue; and/or (c) have a desirable resorption profile that may be adjusted to account for the needs of a range of applications requiring the presence of a stent for different lengths of time or for the elution of therapeutics.

For example, in accordance with one preferred embodiment of the present invention, a medical device is disclosed, comprising an inherently radiopaque, biocompatible, bioresorbable polymer, including homogeneous polymers, copolymers and blends thereof, wherein the polymer comprises one or more recurring units of the Formula (XV):

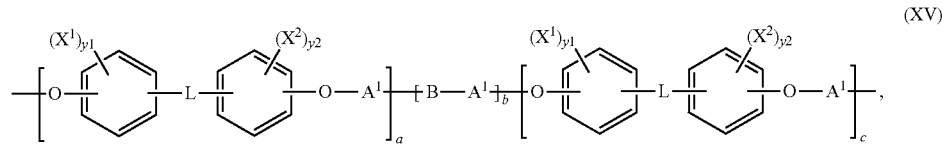

wherein:

$X$, $X^2$, y1, y2, L, B, and $A^1$ are each independently as defined above; and a, b and c may range from 0 to 1, with a normalized sum a+b+c=1.

Preferably, $X^1$, $X^2$, y1, and y2 in Formula (XV) are selected so that $X^1$ and $X^2$ are present in an amount that is effective to render the polymer radiopaque. For example, in an embodiment, the sum of y1 and y2 in Formula (XV) is at least one. In another embodiment, B in Formula (XV) is an aliphatic linear or branched diol or a poly(alkylene glycol) unit.

Examples of preferred copolymers include those of the Formula (XVIa), (XVIb) and (XVIc), as follows:

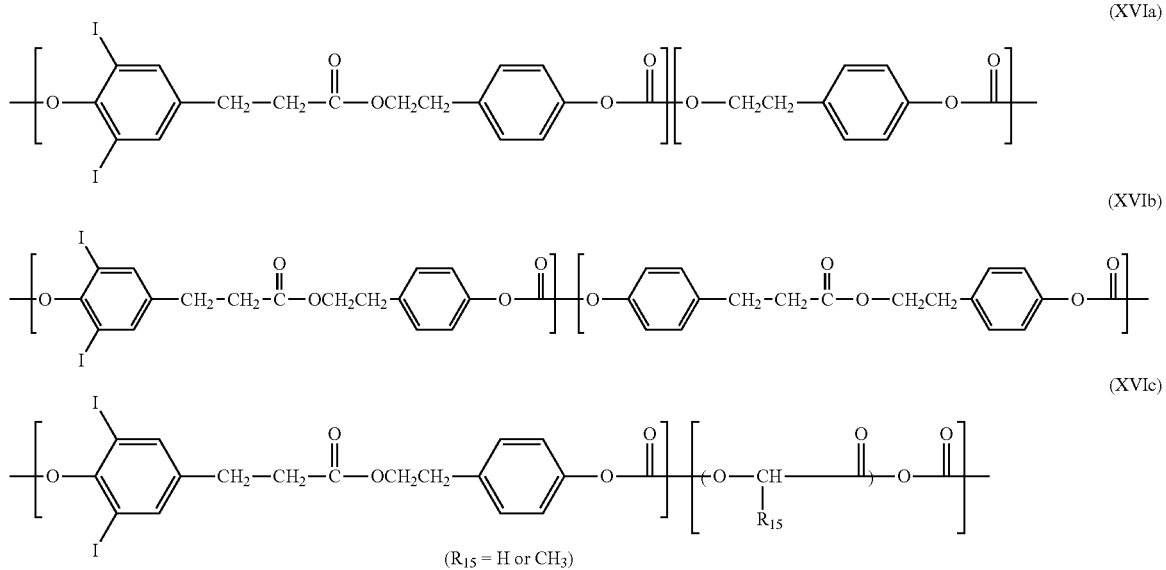

Halogenation of the aromatic rings may be accomplished as described in the examples below, and by conventional methods as detailed in U.S. Pat. No. 6,475,477; herein incorporated in its entirety by reference and particularly for the purpose of describing methods of halogenating monomers. Preferred polymers are sufficiently halogenated to render the resulting polymers radiopaque, e.g., y1 and y2 in any of the formulas described herein may independently be 0, 1, 2, 3 or 4. Halogenation of aromatic rings is preferred. In an embodiment, the sum of y1 and y2 is at least one. Various other groups within the polymer may also be halogenated.

It is surprisingly discovered that after replacement of the amide bond with ester bond, which would be expected to reduce inter-chain hydrogen bonding, in various embodiments the resulting polymer has a higher glass temperature and melting temperature. It is also unexpected that various polymers prepared from tyrosol-derived monomers are semi-crystalline and possess mechanical strength suitable for high strength applications.

Monomer and Polymer Syntheses

The polymers described herein (including, e.g., polymers comprising a recurring unit selected from the group of recurring units represented by Formula (I), Formula (Ia), Formula (Ib), Formula (Ic), Formula (Id), Formula (II), Formula (IIb), Formula (IIc), Formula (IId), Formula (VII), Formula (VIII), Formula (VIIIa), Formula (VIIIb), Formula (VIIIc), Formula (VIIId), Formula (VIIIe), Formula (IX), Formula (X), Formula (XI), Formula (XII), Formula (XIII), Formula (XIV), Formula (XV), Formula (XVIa), Formula (XVIb) and Formula (XVIc)) may be synthesized by various conventional reactions known in the art.

For example, the diphenolic monomer compounds can be reacted with aliphatic or aromatic dicarboxylic acids in a carbodiimide-mediated direct polyesterification using DPTS as a catalyst to form aliphatic or aromatic polyarylates. Examples of dicarboxylic acids suitable for the polymerization to form polyarylates have the structure of Formula (XVII):

$$HO-\overset{O}{\underset{}{C}}-R^{14}-\overset{O}{\underset{}{C}}-OH \qquad (XVII)$$

in which, for the aliphatic polyarylates, $R^{14}$ is selected from saturated and unsaturated, substituted and unsubstituted alkyl or alkylaryl groups containing up to 18 carbon atoms, and preferably from 2 to 12 carbon atoms. For the aromatic polyarylates, $R^{14}$ is selected from aryl groups containing up to 18 carbon atoms and preferably from 6 to 12 carbon atoms. In some embodiments, $R^{14}$ is defined as above for $R^8$.

$R^{14}$ is preferably selected so that the dicarboxylic acids employed as starting materials are either important naturally-occurring metabolites or highly biocompatible compounds. Examples of preferred aliphatic dicarboxylic acid starting materials are described elsewhere herein.

The polyarylates can also be prepared by the method disclosed by Higashi et al., J. Polym. Sci.: Polym. Chem. Ed., 21, 3233-9 (1983) using arylsulfonyl chloride as the condensing agent, by the process of Higashi et al., J. Polym. Sci.: Polym. Chem. Ed., 21, 3241-7 (1983) using diphenyl chlorophosphate as the condensing agent, by the process of Higashi et al., J. Polym. Sci.: Polym. Chem. Ed., 24, 97-102 (1986) using thionyl chloride with pyridine as the condensing agent, or by the process of Elias, et al., Makromol. Chem., 182, 681-6 (1981) using thionyl chloride with triethylamine. A preferred polyesterification procedure is the method disclosed by Moore et al., Macromol., 23, 65-70 (1990) utilizing carbodiimide coupling reagents as the condensing agents with the specially designed catalyst DPTS.

A particularly preferred polyesterification technique modifies the method of Moore to utilize an excess of the carbodiimide coupling reagent. This technique tends to produce aliphatic polyarylates having molecular weights greater than those obtained by Moore. Essentially any carbodiimide commonly used as a coupling reagent in peptide chemistry can be used as a condensing agent in the preferred polyesterification process. Such carbodiimides are well-known and disclosed in Bodanszky, Practice of Peptide Synthesis (Springer-Verlag, New York, 1984) and include dicyclohexylcarbodiimide, diisopropylcarbodiimide, 1-(3-dimethylaminopropyl)-3-ethyl carbodiimide hydrochloride, N-cyclohexyl-N'-(2'-morpholinoethyl)carbodiimide-metho-p-toluene sulfonate, N-benzyl-N'-3'-dimethyl-aminopropyl-carbodiimide hydrochloride, 1-ethyl-3-(3-dimethylamino-propyl)-carbodiimide methiodide, N-ethylcarbodiimide hydrochloride, and the like. The preferred carbodiimides are dicyclohexyl carbodiimide and diisopropylcarbodiimide.

An esterification reaction mixture can generally be formed by contacting exactly equimolar quantities of the diphenol and the dicarboxylic acid in a solvent for the diphenol and the dicarboxylic acid. Suitable solvents include methylene chloride, tetrahydrofuran, dimethylformamide, chloroform, carbon tetrachloride and N-methyl pyrrolidinone. It is not necessary to bring all reagents into complete solution prior to initiating the polyesterification reaction, although the polymerization of slightly soluble monomers such as desaminotyrosyltyrosine ethyl ester and succinic acid will typically yield higher molecular weight polymers when the amount of solvent is increased. The reaction mixture can also be heated gently to aid in the partial dissolution of the reactants.

The polyarylates can be worked up and isolated by known methods commonly employed in the field of synthetic polymers to produce a variety of useful articles with valuable physical and chemical properties, all derived from tissue compatible monomers. The useful articles can be shaped by conventional polymer-forming techniques such as extrusion, compression molding, injection molding, and the like. Molded articles prepared from the polyarylates are useful, inter alia, as degradable biomaterials for medical implant applications. Such applications include the use of the molded articles as vascular grafts and stents, bone plates, sutures, implantable sensors, barriers for surgical adhesion prevention, implantable drug delivery devices and other therapeutic aids and articles which decompose harmlessly within a known period of time.

Synthetic Schemes 1-4 illustrate the preparation of various types of phenolic monomers useful for the making polymers containing recurring units of the Formula (I). One of ordinary skill in the art, guided by the disclosure herein, would understand that these synthetic schemes may be readily adapted to prepare phenolic monomers containing pendant side chains such as —N(R$^x$)C(═O)R$^5$, —N(R$^x$)COOR$^6$, —COOR$^7$ and/or —CONR$^x$R$^y$, as defined above.

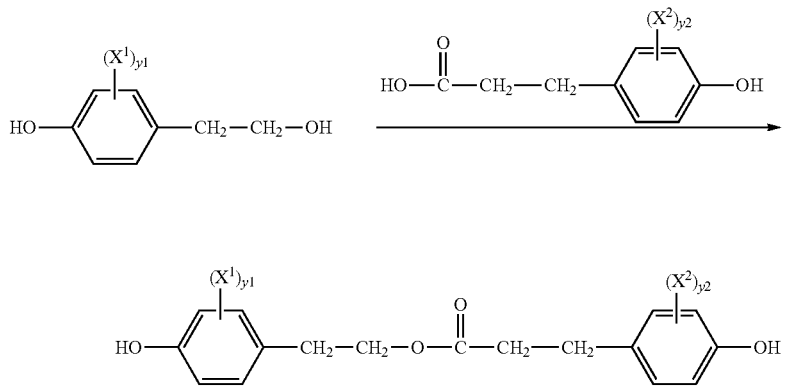

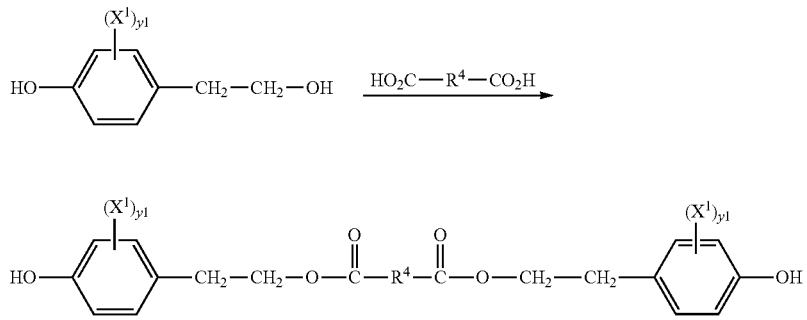

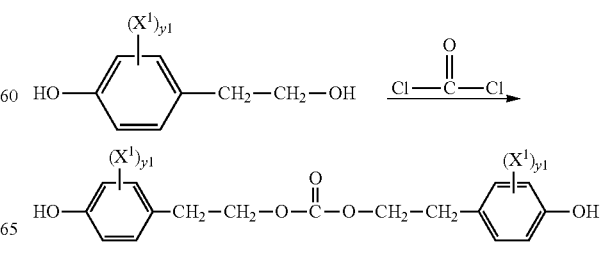

Scheme 4

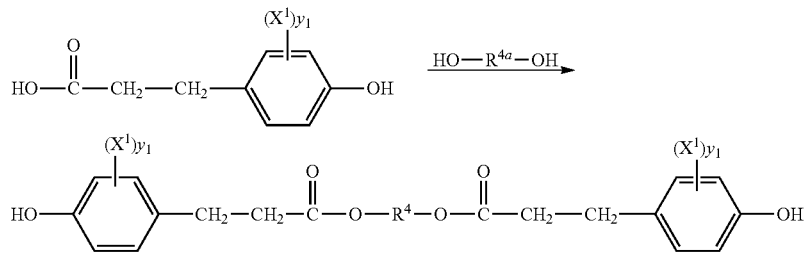

As would be understood by those skilled in the art, a reaction between tyrosol or analogue with phosgene or triphosgene, as illustrated in Scheme 3, would likely give a mixture of three types of dimers linked by a carbonate (—OC(O)O—) group (i.e., "head-head", "tail-tail" and "head-tail") and/or the corresponding polymers, depending on the reaction conditions employed. Therefore, in some embodiments, the present invention provides preparation of these specific dimers and polymers under controlled conditions, as illustrated in Example 17.

In synthetic Schemes 1-10, $X^1$, $X^2$, y1, y2, $R^4$, $R^{4a}$ and $R^8$ are as defined above. In various embodiments of the monomers and polymers described herein, $R^4$, $R^{4a}$ and $R^8$ are each independently $C_1$-$C_{30}$ alkyl, e.g., $C_1$-$C_6$ alkyl, $C_1$-$C_8$ alkyl, $C_1$-$C_{10}$ alkyl, etc. Those skilled in the art will appreciate the extent to which variables (e.g., $X^1$ and $X^2$, and y1 and y2, respectively) may be used interchangeably in the various formulae and schemes provided herein when the depicted structures are symmetrical. Thus, $X^1$ (and $X^2$) may be a halogen, which at each occurrence independently may be selected from iodo, bromo, chloro, and fluoro. Preferably, the halogen is iodo or bromo. Halogenation may be performed by conventional reactions known in the art. For instance, iodination may be performed on aryl rings by treatment with KI, ICl, IF, benzyltrimethylammonium dichloroiodate, or I2 in the presence of copper salts. Similarly, bromination may be performed on aryl rings by treatment with bromine in the presence of a catalyst, such as iron. Other brominating reagents include HOBr and bromo amides. The above synthetic schemes are simplified for illustration purpose. Many variants can be obtained using similar synthetic strategies known to a person of skill in the art, for example, in Scheme 5:

Scheme 5

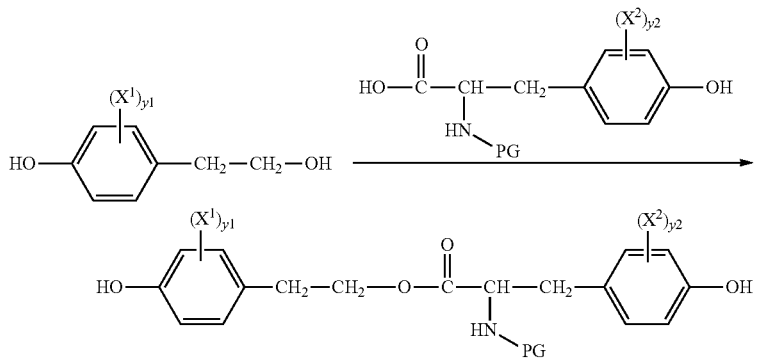

The coupling of the acid and the alcohol may also be performed by conventional reactions known in the art. Standard coupling reagents, including EDCI, HBTU, HOBt, and the like, may be used for activation of the reactants. Examples of synthesis of these polymers are illustrated in the following synthetic Schemes 6-9:

Scheme 6

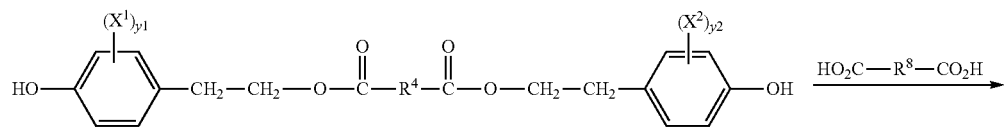

-continued

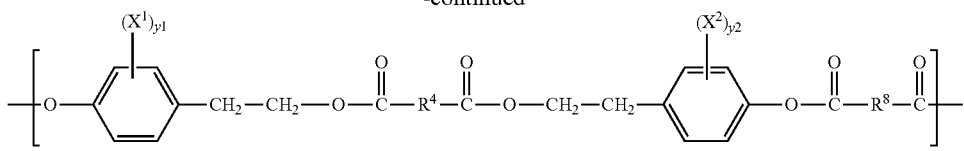

Scheme 7

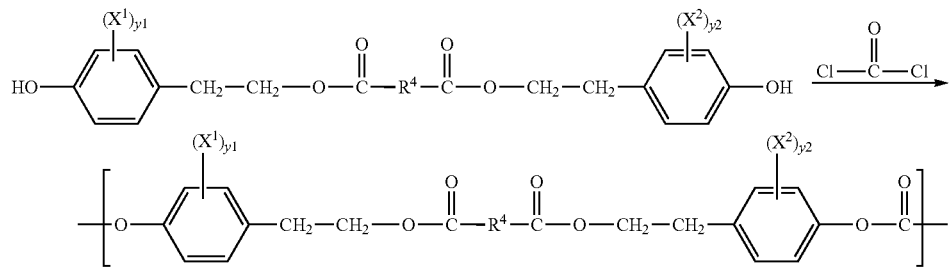

Scheme 8

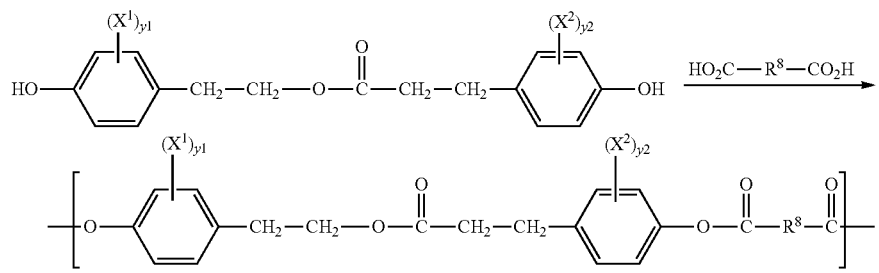

Scheme 9

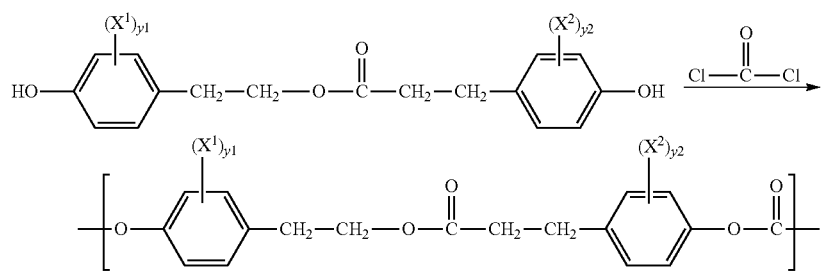

In some embodiments the polymers described herein contain phosphorus. The versatility of these polymers may come from the versatility of the phosphorus atom, which is known for a multiplicity of reactions. Its bonding may involve the 3p orbitals or various 3s-3p hybrids; spd hybrids are also possible because of the accessible of orbitals. Thus, the physico-chemical properties of the poly(phosphoesters) may be readily changed by varying either the R or R' group. The biodegradability of the polymer is due primarily to the physiologically labile phosphoester bond in the backbone of the polymer. By manipulating the backbone or the sidechain, a wide range of biodegradation rates are attainable.

As those skilled in the art would appreciate, when a monomer has an unsymmetrical structure having two equally or similarly reactive functional groups for polymerization, the polymers formed would largely contain the monomeric units in random orders. Such examples include, but are not limited to, the polymerization reactions illustrated in Schemes 6-9 above.

Synthetic Schemes 10-11 below illustrate the syntheses of poly(phosphonates) and poly(phosphates), respectively.

Scheme 10

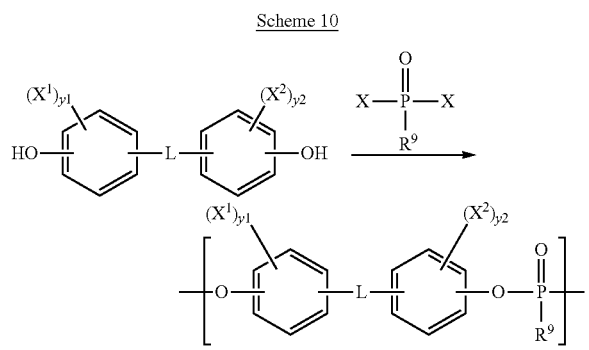

Scheme 11

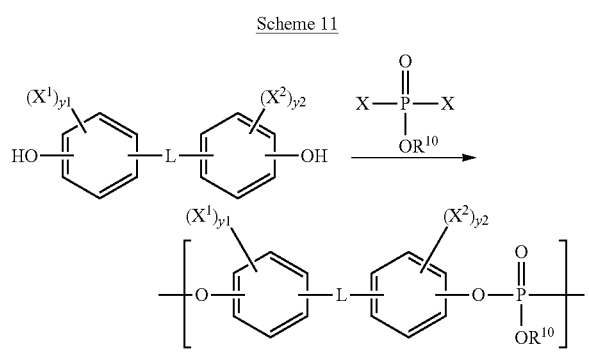

In Schemes 10-13, X is Cl or Br, and $X^1$, $X^2$, y1, y2, L, $R^9$ and $R^{10}$ are as defined above. For example, poly(phosphates) may be prepared by a dehydrochlorination between a phosphodichloridate and a diol according to the following synthetic Scheme 12:

Scheme 12

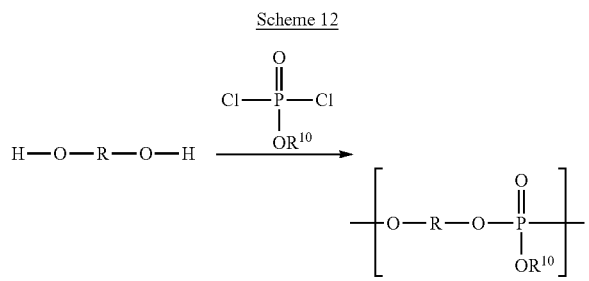

Poly(phosphonates) may be prepared by a similar condensation between appropriately substituted dichlorides and diols.

Poly(phosphites) may be prepared from glycols in a two-step condensation reaction. A 20% molar excess of a dimethylphosphite is preferably used to react with the glycol, followed by the removal of the methoxyphosphonyl end groups in the oligomers by high temperature. An advantage of melt polycondensation is that it avoids the use of solvents and large amounts of other additives, thus making purification more straightforward. It may also provide polymers of reasonably high molecular weight. Polymerization may also be carried out in solution. A chlorinated organic solvent may be used, such as chloroform, dichloromethane, or dichloroethane. To achieve high molecular weights, the solution polymerization is preferably run in the presence of equimolar amounts of the reactants and, more preferably, a stoichiometric amount of an acid acceptor or a Lewis acid-type catalyst. Useful acid acceptors include tertiary amines such as pyridine or triethylamine. Examples of useful Lewis acid-type catalysts include magnesium chloride and calcium chloride. The product may be isolated from the solution by precipitation in a non-solvent and purified to remove the hydrochloride salt by conventional techniques known to those of ordinary skill in the art, such as by washing with an aqueous acidic solution, e.g., dilute HCl.

Halogenated phenolic monomers may also be polymerized to form polyiminocarbonates as illustrated in synthetic Scheme 13:

Scheme 13

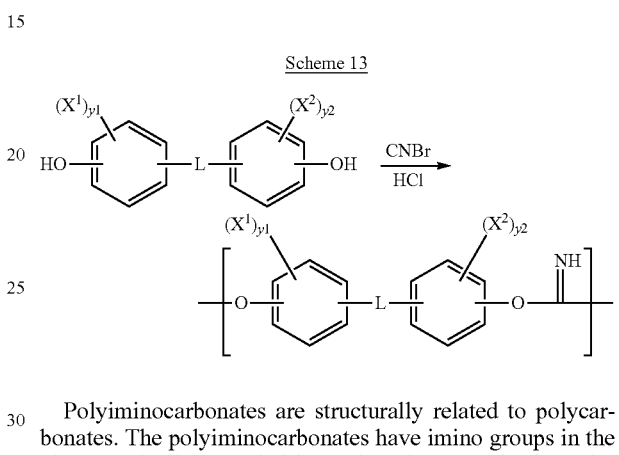

Polyiminocarbonates are structurally related to polycarbonates. The polyiminocarbonates have imino groups in the places typically occupied by carbonyl oxygen in the polycarbonates. Thus, the polyiminocarbonates have linkages according to the formula:

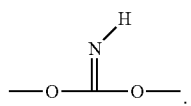

Inclusion of iminocarbonate linkages may impart a significant degree of hydrolytic instability to the polymer. The polyiminocarbonates have desirable mechanical properties akin to those of the corresponding polycarbonates.

Starting materials described herein are available commercially, are known, or may be prepared by methods known in the art. Additionally, starting materials not described herein are available commercially, are known, or may be prepared by methods known in the art.

Starting materials may have the appropriate substituents to ultimately give desired products with the corresponding substituents. Alternatively, substituents may be added at any point of synthesis to ultimately give desired products with the corresponding substituents.

The synthetic schemes illustrated herein show methods that may be used to prepare the compounds of preferred embodiments. One skilled in the art will appreciate that a number of different synthetic reaction schemes may be used to synthesize the compounds of preferred embodiments. Further, one skilled in the art will understand that a number of different solvents, coupling agents and reaction conditions may be used in the synthetic reactions to yield comparable results.

One skilled in the art will appreciate variations in the sequence and, further, will recognize variations in the appropriate reaction conditions from the analogous reactions shown or otherwise known which may be appropriately used in the processes above to make the compounds of preferred embodiments.

In the processes described herein for the preparation of the compounds of preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1999.

The products of the reactions described herein can be isolated by conventional means such as extraction, distillation, chromatography, and the like.

The salts of the compounds described herein can be prepared by reacting the appropriate base or acid with a stoichiometric equivalent of the compound.

In some embodiments, the polymer comprises poly(ether carbonate) with tyrosol-bioactive moiety. A desaminotyrosyl-tyrosine dipeptide can be combined with the PEG in methylene chloride and phosgene can be added as a solution in toluene. The reaction would be completed in around 9 minutes. In some embodiments, this reaction is carried out for from 1-60 minutes. In an embodiment, the polymer comprises poly(tyrosine carbonate) pendant bioactive moiety groups. In some embodiments, the polymer comprises poly(ether carbonate) tyrosine-diol copolymer with a bioactive moiety in the backbone. In some embodiments, the polymer comprises poly(ether carbonate) tyrosine-diol copolymer with a pendant bioactive moiety. In some embodiments, the polymer comprises poly(ether ester) tyrosine-bioactive moiety-diacid copolymer. In some embodiments, the polymer comprises poly(imino carbonate) tyrosine-bioactive moiety-copolymer. In some embodiments, the polymer comprises poly(imino tyrosine) with pendant PEG groups.

In another aspect the present invention provides a medical device that comprises a polymer and/or polymer composition as described herein. For example, an embodiment provides a stent that comprises a polymer composition as described herein. Another embodiment provides a method of treating a body lumen, comprising deploying the stent within the body lumen. These and other embodiments are described in greater detail below.

Definitions

The term "biodegradable," as used herein, refers to a property of polymer whose molecular weight goes down because of hydrolysis or enzymatic reactions under physiological conditions such that the polymer is transformed into lower molecular weight oligomers in a period not to exceed four (4) years.

The term "oligomer," as used herein, refers to a hydrolyzed product of a polymer, whose molecular weight is less than 10% of the original polymer.

The terms "alkyl", "alkylene" and similar terms have the usual meaning known to those skilled in the art and thus may be used to refer to straight or branched hydrocarbon chain fully saturated (no double or triple bonds) hydrocarbon group. Terminal alkyl groups, e.g., of the general formula $-C_nH_{2n+1}$, may be referred to herein as "alkyl" groups, whereas linking alkyl groups, e.g., of the general formula $-(CH_2)_n-$, may be referred to herein as "alkylene" groups.

The alkyl group may have 1 to 50 carbon atoms (whenever it appears herein, a numerical range such as "1 to 50" refers to each integer in the given range; e.g., "1 to 50 carbon atoms" means that the alkyl group may consist of 1 carbon atom, 2 carbon atoms, 3 carbon atoms, etc., up to and including 50 carbon atoms, although the present definition also covers the occurrence of the term "alkyl" where no numerical range is designated). The alkyl group may also be a medium size alkyl having 1 to 30 carbon atoms. The alkyl group could also be a lower alkyl having 1 to 5 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl and the like.

The alkyl group may be substituted or unsubstituted. When substituted, the substituent group(s) is(are) one or more group(s) individually and independently selected from alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. Wherever a substituent is described as being "optionally substituted" that substitutent may be substituted with one of the above substituents.

An "alkylaryl" is an aryl group connected, as a substituent, via an alkylene group. The alkylene and aryl group of an aralkyl may be substituted or unsubstituted. Examples include but are not limited to benzyl, substituted benzyl, 2-phenylethyl, 3-phenylpropyl, and naphtylalkyl. In some cases, the alkylene group is a lower alkylene group. An alkylaryl group may be substituted or unsubstituted.

As noted above, alkyl groups may link together other groups, and in that context may be referred to as alkylene groups. Alkylene groups are thus biradical tethering groups, forming bonds to connect molecular fragments via their terminal carbon atoms. Examples include but are not limited to methylene ($-CH_2-$), ethylene ($-CH_2CH_2-$), propylene ($-CH_2CH_2CH_2-$), and butylene ($-(CH_2)_4-$) groups. An alkylene group may be substituted or unsubstituted.

The terms "alkenyl", "alkenylene" and similar terms have the usual meaning known to those skilled in the art and thus may be used to refer to an alkyl or alkylene group that contains in the straight or branched hydrocarbon chain containing one or more double bonds. An alkenyl group may be unsubstituted or substituted. When substituted, the substituent(s) may be selected from the same groups disclosed above with regard to alkyl group substitution unless otherwise indicated.

An "amide" is a chemical moiety with formula $-(R)_n-C(O)NHR'$ or $-(R)_n-NHC(O)R'$, where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug. An "amide linkage" is an amide group (—C(O)NH—) that links two chemical moieties to one another.

Any amine, hydroxy, or carboxyl side chain on the compounds disclosed herein can be esterified or amidified. The procedures and specific groups to be used to achieve this end are known to those of skill in the art and can readily be found in reference sources such as Greene and Wuts, Protective Groups in Organic Synthesis, 3rd Ed., John Wiley & Sons, New York, N.Y., 1999, which is incorporated by reference herein in its entirety.

As used herein, "aryl" refers to a carbocyclic (all carbon) ring or two or more fused rings (rings that share two adjacent carbon atoms) that have a fully delocalized pi-electron system. Examples of aryl groups include, but are not limited to, benzene, naphthalene and azulene. An aryl group may be substituted or unsubstituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalo-methanesulfonamido, and amino, including mono- and di-substituted amino groups, and the protected derivatives thereof. When substituted, substituents on an aryl group may form a non-aromatic ring fused to the aryl group, including a cycloalkyl, cycloalkenyl, cycloalkynyl, and heterocyclyl.

As used herein, "heteroalkyl" refers to an alkyl group where one or more carbon atoms has been replaced with a heteroatom, that is, an element other than carbon, including but not limited to, nitrogen, oxygen and sulfur.

The terms "heteroalkyl", "heteroalkylene," and similar terms have the usual meaning known to those skilled in the art and thus may be used to refer to an alkyl group or alkylene group as described herein in which one or more of the carbons atoms in the backbone of alkyl group or alkylene group has been replaced by a heteroatom such as nitrogen, sulfur and/or oxygen. Likewise, the term "heteroalkenylene" may be used to refer to an alkenyl or alkenylene group in which one or more of the carbons atoms in the backbone of alkyl group or alkylene group has been replaced by a heteroatom such as nitrogen, sulfur and/or oxygen.

As used herein, "heteroaryl" refers to an aryl group where one or more carbon atoms has been replaced with a heteroatom, that is, an element other than carbon, including but not limited to, nitrogen, oxygen and sulfur.

For convenience and conciseness, sometimes the terms "alkyl", "alkenyl", "alkynyl", "aryl", "heteroaryl", and "alkylaryl", or the like, may be used to refer to the corresponding linking groups when they serve to connect two moieties of a molecule, either monomeric or polymeric, which should be readily understood by those skilled in the art. That is, on such occasions, "alkyl" should be interpreted as "alkylene"; "alkenyl" should be interpreted as "alkenylene"; "aryl" should be interpreted as "arylene"; and so on.

A "heavy atom" is an atom that, when attached to a polymer, renders the polymer easier to detect by an imaging technique as compared to a polymer that does not contain the heavy atom. Since many polymers contain relatively low atomic number atoms such as hydrogen, carbon, nitrogen, oxygen, silicon and sulfur, in most cases heavy atoms have an atomic number of 17 or greater. Preferred heavy atoms have an atomic number of 35 or greater, and include bromine, iodine, bismuth, gold, platinum tantalum, tungsten, and barium.

A "hydrocarbon" is an organic compound consisting entirely of hydrogen and carbon. Examples of hydrocarbons include unsubstituted alkyl groups, unsubstituted aryl groups, and unsubstituted alkylaryl groups. Any substitution to an alkyl group, aryl group, or alkylaryl group in a hydrocarbon would only comprise carbon and/or hydrogen atoms.

As used herein, the terms "macromer", "macromeric" and similar terms have the usual meaning known to those skilled in the art and thus may be used to refer to oligomeric and polymeric materials that are functionalized with end groups that are selected so that the macromers can be copolymerized with other macromers or monomers. A wide variety of macromers and methods for making them are known to those skilled in the art. Examples of suitable macromers include hydroxy endcapped polylactic acid macromers, hydroxy endcapped polyglycolic acid macromers, hydroxy endcapped poly(lactic acid-co-glycolic acid) macromers, hydroxy endcapped polycaprolactone macromers, poly(alkylene diol) macromers, hydroxy end-capped poly(alkylene oxide) macromers and hydroxy endcapped polydioxanone macromers.

As used herein, the terms "polymer", "polymeric" and similar terms have the usual meaning known to those skilled in the art and thus may be used to refer to homopolymers, copolymers (e.g., random copolymer, alternating copolymer, block copolymer, graft copolymer) and mixtures thereof. The repeating structural units of polymers may also be referred to herein as recurring units.

As used herein, the term "molecular weight" has the usual meaning known to those skilled in the art and thus reference herein to a polymer having a particular molecular weight will be understood as a reference to a polymer molecular weight in units of Daltons. Various techniques known to those skilled in the art, such as end group analysis (e.g., by $^1$H NMR) and high pressure size exclusion chromatography (HPSEC, also known as gel permeation chromatography, "GPC"), may be used to determine polymer molecular weights. In some cases the molecular weights of polymers are further described herein using the terms "number average" molecular weight (Mn) and/or "weight average" molecular weight (Mw), both of which terms are likewise expressed in units of Daltons and have the usual meaning known to those skilled in the art.

Unless otherwise indicated, when a substituent is deemed to be "optionally substituted," it is meant that the substituent is a group that may be substituted with one or more group(s) individually and independently selected from alkyl, alkenyl, alkylyl, cycloalkyl, aryl, heteroaryl, heteroalicyclic, hydroxyl, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, above.

The terms "radiopaque", "radio-opaque", "radiopacity", "radio-opacity", "radiopacifying" and similar terms have the usual meaning known to those skilled in the art and thus may be used to refer to polymer compositions that have been rendered easier to detect using medical imaging techniques (e.g., by X-ray and/or during fluoroscopy) being the incorporation of heavy atoms into the polymer composition. Such incorporation may be by mixing, e.g., by mixing an effective amount of a radiopacifying additive such as barium salt or complex, and/or by attachment of effective amounts of heavy atoms to one or more of the polymers in the polymer composition.

In certain configurations, polymer compositions may be inherently radiopaque. The term "inherently radiopaque" is used herein to refer to a polymer to which a sufficient number of heavy atoms are attached by covalent or ionic bonds to render the polymer radiopaque. This meaning is consistent with the understanding of those skilled in the art, see, e.g., U.S. Patent Publication No. 2006/0024266, which is hereby incorporated by reference for all purposes, including for the particular purpose of describing radiopaque polymeric materials.

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents.

Unless otherwise indicated, when a substituent is deemed to be "optionally substituted," or "substituted" it is meant that the substituent is a group that may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. Similarly, the term "optionally ring-halogenated" may be used to refer to a group that optionally contains one or more (e.g., one, two, three or four) halogen substituents on the aryl and/or heteroaryl ring. The protecting groups that may form the protective derivatives of the above substituents are known to those of skill in the art and may be found in references such as Greene and Wuts, Protective Groups in Organic Synthesis, 3$^{rd}$ Ed., John Wiley & Sons, New York, N.Y., 1999, which is hereby incorporated by reference in its entirety.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition it is understood that, in any compound having one or more double bond(s) generating geometrical isomers that can be defined as E or Z each double bond may independently be E or Z a mixture thereof. Likewise, all tautomeric forms are also intended to be included.

The following abbreviations are used to identify various iodinated compounds. TE stands for tyrosine ethyl ester, DAT stands for desaminotyrosine and DTE for desaminotyrosyl tyrosine ethyl ester. PTE stands for hydroxy-phenoxy-1-oxoethyl tyrosine ethyl ester. Ty stands for tyrosol. The polymer obtained by phosgenation of DTE is denoted as poly(DTE carbonate). An "I" before the abbreviation shows mono-iodination (e.g. ITE stands for mono-iodinated TE) and an I$_2$ before the abbreviation shows di-iodination (e.g. I$_2$DAT stands for di-iodinated DAT). In DTE, if the "I" is before D, it means the iodine is on DAT and if "I" is after D, it means the iodine is on the tyrosine ring (e.g. DI$_2$TE stands for DTE with 2 iodine atoms on the tyrosine ring). The following diagram illustrates this nomenclature further.

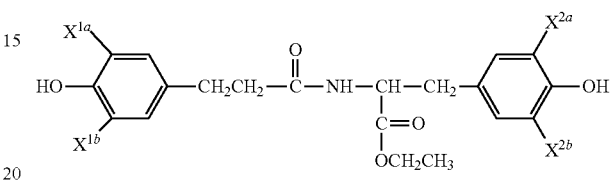

General Structure of Iodinated DTE Monomer
IDTE: $X^{1a}$=I, $X^{1b}$=H, $X^{2a}$=H, $X^{2b}$=H.
I$_2$DTE: $X^{1a}$=I, $X^{1b}$=I, $X^{2a}$=H, $X^{2b}$=H
DI$_2$TE: $X^{1a}$=H, $X^{1b}$=H, $X^{2a}$=I, $X^{2b}$=I
IDITE: $X^{1a}$=I, $X^{1b}$=H, $X^{2a}$=I, $X^{2b}$=H For PTE, PTH, IPTE, I$_2$PTE, PI$_2$TE, etc., the DAT CH$_2$CH$_2$ is replaced with OCH$_2$.

As used herein, the abbreviations for any protective groups, amino acids and other compounds are, unless indicated otherwise, in accord with their common usage, recognized abbreviations, or the IUPAC-IUP Commission on Biochemical Nomenclature (See, Biochem. 11:942-944 (1972)).

The term "halogen atom," as used herein, means any one of the radio-stable atoms of column 7 of the Periodic Table of the Elements, e.g., fluorine, chlorine, bromine, or iodine, with bromine and iodine being preferred.

The term "ester" refers to a chemical moiety with formula —(R)$_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1. An "ester linkage" is an ester group that links two chemical moieties to one another.

The terms "purified," "substantially purified," and "isolated" as used herein refer to compounds disclosed herein being substantially free of other, dissimilar compounds with which the compounds of the invention are normally associated in their natural state, so that the compounds of the invention comprise at least 0.5%, 1%, 5%, 10%, or 20%, and most preferably at least 50% or 75% of the mass, by weight, of a given sample.

It is understood that the polymers described herein may be used in accordance with preferred aspects of the invention as a homogeneous polymer, as a copolymer, and/or as a polymer blend. Accordingly, for example, reference herein to a polymer of the Formula (I) is understood to be a reference to a polymer that comprises a recurring unit of the Formula (I), which may be a homopolymer, copolymer or blend. Likewise, as another example, reference herein to a polymer of the Formula (Ia) is understood to be a reference to a polymer that comprises a recurring unit of the Formula (Ia), which may be a homopolymer, copolymer or blend.

Although the inventors do not wish to be bound by or to any particular theory of operation, the inventors believe that the beneficial combination of properties associated with the medical devices of the present invention are attributable, at least in part, to certain characteristics of the polymers of formula (Ia), from which the devices are made.

The bioresorbable, inherently radiopaque stents disclosed in accordance with preferred embodiments of the present invention may be used, for example, to temporarily treat a blood vessel as in traditional applications which generally include delivery through a catheter.

In some embodiments polymers prepared from sufficient amounts of the monomeric starting materials described herein and having at least one bromine- or iodine-substituted aromatic ring are radio-opaque, such as the polymers prepared from radiopaque diphenol compounds prepared according to the disclosure of U.S. Pat. No. 6,475,477, as well as he disclosure of co-pending and commonly-owned U.S. patent application Ser. No. 10/592,202, the disclosures of both of which are incorporated herein by reference. The iodinated and brominated diphenol monomers of the present invention can also be employed as radio-opacifying, biocompatible non-toxic additives for other polymeric biomaterials.

Bromine and iodine substituted aromatic monomers of the present invention can be prepared by well-known iodination and bromination techniques that can be readily employed by those of ordinary skill in the art in view of the guidance provided herein without undue experimentation. In some embodiments, the halogenated aromatic compounds from which the halogenated aromatic monomers of the present invention are prepared typically undergo ortho-directed halogenation. The term, "ortho-directed", is used herein to designate orientation of the halogen atom(s) relative to the phenoxy alcohol group.

The polymers described herein include polymers prepared by polymerizing Formula III monomers having pendent free carboxylic acid groups. However, it is not possible to polymerize polymers having pendent free carboxylic acid groups from corresponding monomers with pendent free carboxylic acid groups without cross-reaction of the free carboxylic acid group with the co-monomer. Accordingly, polymers in accordance with the present invention having pendent free carboxylic acid groups are prepared from homopolymers and copolymers of benzyl and tert-butyl ester monomers of the present invention.

The benzyl ester homopolymers and copolymers may be converted to corresponding free carboxylic acid homopolymers and copolymers through the selective removal of the benzyl groups by the palladium catalyzed hydrogenolysis method disclosed by co-pending and commonly owned U.S. Pat. No. 6,120,491, the disclosure of which is incorporated herein by reference.

The tert-butyl ester homopolymers and copolymers may be converted to corresponding free carboxylic acid homopolymers and copolymers through the selective removal of the tert-butyl groups by the acidolyis method disclosed by the above-referenced U.S. patent application Ser. No. 10/592, 202, also incorporated herein by reference.

After polymerization, appropriate work up of the polymers in accordance with preferred embodiments of the present invention may be achieved by any of a variety of known methods commonly employed in the field of synthetic polymers to produce a variety of useful articles with valuable physical and chemical properties, all derived from tissue compatible monomers. The useful articles can be shaped by conventional polymer-forming techniques such as extrusion, compression molding, injection molding, solvent casting, spin casting, wet spinning, combinations of two or more thereof, and the like. Shaped articles prepared from the polymers are useful, inter alia, as degradable biomaterials for medical implant applications. Such applications include the use of shaped articles as vascular grafts and stents.

Polymers according to the present invention also include polyethers, polyurethanes, poly(carbamates), poly(thiocarbonates), poly(carbonodithionates) and poly(thiocarbamates), which may be prepared from the diphenol compounds of the present invention in accordance with known methods.

Random or block copolymers of the polymers of the present invention with a poly(alkylene oxide) may be prepared according to the method disclosed in U.S. Pat. No. 5,658,995, the disclosure of which is also incorporated by reference. The poly(alkylene oxide) is preferably a poly(ethylene glycol) block/unit typically having a molecular weight of less than about 10,000 per unit. More typically, the poly(ethylene glycol) block/unit has a molecular weight less than about 4000 per unit. The molecular weight is preferably between about 1000 and about 2000 per unit.

The molar fraction of poly(ethylene glycol) units in block copolymers may range from greater than zero to less than 1, and is typically greater than zero up to about 0.5, inclusive. More preferably, the molar fraction is less than about 0.25 and yet more preferably, less than about 0.1. In a more preferred variations, the molar fraction may vary from greater than about 0.001 to about 0.08, and most preferably, between about 0.025 and about 0.035.

Unless otherwise indicated, the molar fractions reported herein are based on the total molar amount of poly(alkylene glycol) and non-glycol units in the polymers.

After polymerization, appropriate work up of the polymers in accordance with preferred embodiments of the present invention may be achieved by any of a variety of known methods commonly employed in the field of synthetic polymers to produce a variety of useful articles with valuable physical and chemical properties, all derived from tissue compatible monomers. The useful articles can be shaped by conventional polymer thermo-forming techniques such as extrusion and injection molding when the degradation temperature of the polymer is above the glass transition or crystalline melt temperature, or conventional non-thermal techniques can be used, such as compression molding, injection molding, solvent casting, spin casting, wet spinning. Combinations of two or more methods can be used. Shaped articles prepared from the polymers are useful, inter alia, as degradable biomaterials for medical implant applications.

Those skilled in the art will recognize that by appropriate selection of variable groups, embodiments of the compounds described above can be a hydroxyphenyl-alkanoic acid, such as desaminotyrosyl tyrosine (DAT), or a hydroxyphenylalkenoic acid. When the compound of the formula HX$^3$-D$^1$-X$^4$H is a diol, the two compounds may be reacted in an acid catalyzed Fischer esterification reaction, illustrated generally as follows:

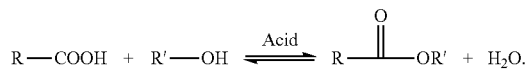

Because this reaction is reversible, removing water from the reaction mixture shifts the equilibrium to the right. Water removal is usually accomplished by way of azeotropic distillation, however other techniques known in the art may be employed as well. In instances where azeotropic distillation is desired, the solvent used for the reaction is preferably carefully chosen so that it forms an azeotropic mixture with water. Generally, solvents such as toluene, heptane, chloroform, tetrachloethylene are preferred.

The main advantage of this reaction is that primary and secondary alcohols form esters with carboxylic acids under acid catalysis, whereas the phenolic hydroxy groups are unreactive under these conditions. Thus the carboxylic acid groups of certain compounds, such as the 3-(4-hydroxyphenyl) propionic acid (DAT) and of 3-(3,5-diiodo-4-hydroxyphenyl) propionic acid ($I_2$DAT), can be reacted with primary or secondary alcohols while the phenolic groups remain intact. An example of the foregoing is is generally illustrated in Scheme 4 above, and also as follows in synthetic Scheme 14:

In one embodiment, the medical device is a stent. It is contemplated that a stent may comprise many different types of forms. For instance, the stent may be an expandable stent. In another embodiment, the stent may be configured to have the form of a sheet stent, a braided stent, a self-expanding stent, a woven stent, a deformable stent, or a slide-and-lock stent. Stent fabrication processes may further include two-dimensional methods of fabrication such as cutting extruded sheets of polymer, via laser cutting, etching, mechanical cutting, or other methods, and assembling the resulting cut portions into stents, or similar methods of three-dimensional fabrication of devices from solid forms.

Scheme 14

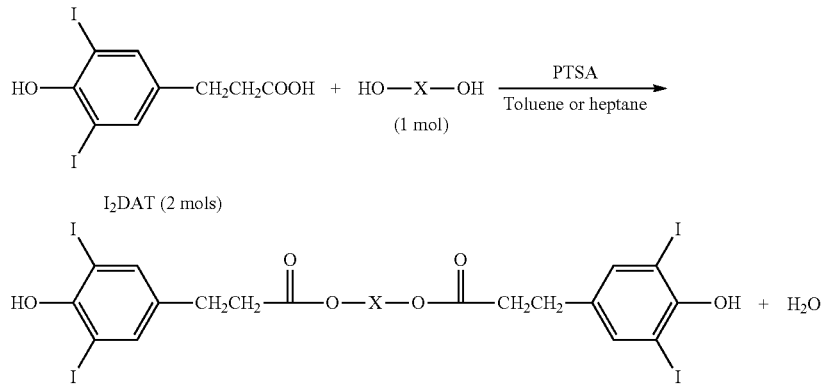

In Scheme 14, X can be $R^{4a}$ as defined above. Polymer compositions as described herein also include polyethers, polyesters, poly-iminocarbonates, polyphosphoesters and polyphosphazines. Those skilled in the art can prepare these polymers using routine experimentation informed by the guidance provided herein. Polyesters, specifically poly(ester amides), may be prepared by the process disclosed by U.S. Pat. No. 5,216,115, the disclosure of which is incorporated by reference, and particularly for the purpose of describing such processes. Polyiminocarbonates may be prepared by the process disclosed by U.S. Pat. No. 4,980,449, the disclosure of which is incorporated by reference, and particularly for the purpose of describing such processes. Polyethers may be prepared by the process disclosed by U.S. Pat. No. 6,602,497, the disclosure of which is incorporated by reference, and particularly for the purpose of describing such processes.

Medical Uses

Various embodiments of the polymer compositions described herein, preferably derived from tissue compatible monomers, may be used to produce a variety of useful articles with valuable physical and chemical properties. The useful articles can be shaped by conventional polymer thermo-forming techniques such as extrusion and injection molding when the degradation temperature of the polymer is above the glass transition or crystalline melt temperature(s), or conventional non-thermal techniques can be used, such as compression molding, injection molding, solvent casting, spin casting, wet spinning. Combinations of two or more methods can be used. Shaped articles prepared from the polymers are useful, inter alia, as biocompatible, biodegradable and/or bioresorbable biomaterials for medical implant applications.

In certain other embodiments, the polymers are formed into coatings on the surface of an implantable device, particularly a stent, made either of a polymer as described herein or another material, such as metal. Such coatings may be formed on stents via techniques such as dipping, spray coating, combinations thereof, and the like. Further, stents may be comprised of at least one fiber material, curable material, laminated material and/or woven material. The medical device may also be a stent graft or a device used in embolotherapy.

The highly beneficial combination of properties associated with preferred embodiments of the polymers described herein means these polymers are well-suited for use in producing a variety of resorbable medical devices besides stents, especially implantable medical devices that are preferably radiopaque, biocompatible, and have various times of bioresorption. For example the polymers are suitable for use in resorbable implantable devices with and without therapeutic agents, device components and/or coatings with and without therapeutic agents for use in other medical systems, for instance, the musculoskeletal or orthopedic system (e.g., tendons, ligaments, bone, cartilage skeletal, smooth muscles); the nervous system (e.g., spinal cord, brain, eyes, inner ear); the respiratory system (e.g., nasal cavity and sinuses, trachea, larynx, lungs); the reproductive system (e.g., male or female reproductive); the urinary system (e.g., kidneys, bladder, urethra, ureter); the digestive system (e.g., oral cavity, teeth, salivary glands, pharynx, esophagus, stomach, small intestine, colon), exocrine functions (biliary tract, gall bladder, liver, appendix, recto-anal canal); the endocrine system (e.g., pancreas/islets, pituitary, parathyroid, thyroid, adrenal and pineal body), the hematopoietic system (e.g., blood and bone marrow, lymph nodes, spleen, thymus, lymphatic vessels); and, the integumentary system (e.g., skin, hair, nails, sweat glands, sebaceous glands).

The polymers described herein can thus be used to fabricate wound closure devices, hernia repair meshes, gastric lap bands, drug delivery implants, envelopes for the implantation of cardiac devices, devices for other cardiovascular applications, non-cardiovascular stents such as biliary stents, esophageal stents, vaginal stents, lung-trachea/bronchus stents, and the like.

In addition, the resorbable polymers are suitable for use in producing implantable, radiopaque discs, plugs, and other devices used to track regions of tissue removal, for example, in the removal of cancerous tissue and organ removal, as well as, staples and clips suitable for use in wound closure, attaching tissue to bone and/or cartilage, stopping bleeding (homeostasis), tubal ligation, surgical adhesion prevention, and the like. Applicants have also recognized that preferred embodiments of the polymers described herein are well-suited for use in producing a variety of coatings for medical devices, especially implantable medical devices.

Further, in some preferred embodiments, the present polymers may be advantageously used in making various resorbable orthopedic devices including, for example, radiopaque biodegradable screws (interference screws), radiopaque biodegradable suture anchors, and the like for use in applications including the correction, prevention, reconstruction, and repair of the anterior cruciate ligament (ACL), the rotator cuff/rotator cup, and other skeletal deformities.

Other devices that can be advantageously formed from preferred embodiments of the polymers described herein, include devices for use in tissue engineering. Examples of suitable resorbable devices include tissue engineering scaffolds and grafts (such as vascular grafts, grafts or implants used in nerve regeneration). The resorbable polymers may also be used to form a variety of devices effective for use in closing internal wounds. For example biodegradable resorbable sutures, clips, staples, barbed or mesh sutures, implantable organ supports, and the like, for use in various surgery, cosmetic applications, and cardiac wound closures can be formed.

Various devices useful in dental applications may advantageously be formed according to embodiments of the described herein. For example devices for guided tissue regeneration, alveolar ridge replacement for denture wearers, and devices for the regeneration of maxilla-facial bones may benefit from being radiopaque so that the surgeon or dentist can ascertain the placement and continuous function of such implants by simple X-ray imaging.

Preferred embodiments of the polymers described herein are also useful in the production of bioresorbable, inherently radiopaque polymeric embolotherapy products for the temporary and therapeutic restriction or blocking of blood supply to treat tumors and vascular malformations, e.g., uterine fibroids, tumors (i.e., chemoembolization), hemorrhage (e.g., during trauma with bleeding) and arteriovenous malformations, fistulas and aneurysms delivered by means of catheter or syringe. Details of embolotherapy products and methods of fabrication in which the polymers described herein may be employed are disclosed in U.S. Patent Publication No. 20050106119 A1, the disclosure of which is incorporated by reference, and particularly for the purpose of describing such products and methods. Embolotherapy treatment methods are by their very nature local rather than systemic and the products are preferably fabricated from the radio-opaque polymers described herein, to permit fluoroscopic monitoring of delivery and treatment.

The polymers described herein are further useful in the production of a wide variety of therapeutic agent delivery devices. Such devices may be adapted for use with a variety of therapeutics including, for example, pharmaceuticals (i.e., drugs) and/or biological agents as previously defined and including biomolecules, genetic material, and processed biologic materials, and the like. Any number of transport systems capable of delivering therapeutics to the body can be made, including devices for therapeutics delivery in the treatment of cancer, intravascular problems, dental problems, obesity, infection, and the like.

A medical device that comprises a polymeric material may include one or more additional components, e.g., a plasticizer, a filler, a crystallization nucleating agent, a preservative, a stabilizer, a photoactivation agent, etc., depending on the intended application. For example, in an embodiment, a medical device comprises an effective amount of at least one therapeutic agent and/or a magnetic resonance enhancing agent. Non-limiting examples of preferred therapeutic agents include a chemotherapeutic agent, a non-steroidal anti-inflammatory, a steroidal anti-inflammatory, and a wound healing agent. Therapeutic agents may be co-administered with the polymeric material. In a preferred embodiment, at least a portion of the therapeutic agent is contained within the polymeric material. In another embodiment, at least a portion of the therapeutic agent is contained within a coating on the surface of the medical device.

Non-limiting examples of preferred chemotherapeutic agents include taxanes, tax-mines, taxols, paclitaxel, dioxorubicin, cis-platin, adriamycin and bleomycin. Non-limiting examples of preferred non-steroidal anti-inflammatory compounds include aspirin, dexa-methasone, ibuprofen, naproxen, and Cox-2 inhibitors (e.g., Rofexcoxib, Celecoxib and Valdecoxib). Non-limiting examples of preferred steroidal anti-inflammatory compounds include dexamethasone, beclomethasone, hydrocortisone, and prednisone. Mixtures comprising one or more therapeutic agents may be used. Non-limiting examples of preferred magnetic resonance enhancing agents include gadolinium salts such as gadolinium carbonate, gadolinium oxide, gadolinium chloride, and mixtures thereof.

The amounts of additional components present in the medical device are preferably selected to be effective for the intended application. For example, a therapeutic agent is preferably present in the medical device in an amount that is effective to achieve the desired therapeutic effect in the patient to whom the medical device is administered or implanted. Such amounts may be determined by routine experimentation. In certain embodiments, the desired therapeutic effect is a biological response. In an embodiment, the therapeutic agent in the medical device is selected to promote at least one biological response, preferably a biological response selected from the group consisting of thrombosis, cell attachment, cell proliferation, attraction of inflammatory cells, deposition of matrix proteins, inhibition of thrombosis, inhibition of cell attachment, inhibition of cell proliferation, inhibition of inflammatory cells, and inhibition of deposition of matrix proteins. The amount of magnetic resonance enhancing agent in a medical devices is preferably an amount that is effective to facilitate radiologic imaging, and may be determined by routine experimentation.

The term "pharmaceutical agent", as used herein, encompasses a substance intended for mitigation, treatment, or prevention of disease that stimulates a specific physiologic (metabolic) response. The term "biological agent", as used herein, encompasses any substance that possesses structural and/or functional activity in a biological system, including without limitation, organ, tissue or cell based derivatives, cells, viruses, vectors, nucleic acids (animal, plant, microbial, and viral) that are natural and recombinant and synthetic in origin and of any sequence and size, antibodies, polynucleotides, oligonucleotides, cDNA's, oncogenes, proteins, peptides, amino acids, lipoproteins, glycoproteins, lipids, carbohydrates, polysaccharides, lipids, liposomes, or other cellular components or organelles for instance receptors and ligands. Further the term "biological agent", as used herein, includes virus, serum, toxin, antitoxin, vaccine, blood, blood component or derivative, allergenic product, or analogous product, or arsphenamine or its derivatives (or any trivalent organic arsenic compound) applicable to the prevention, treatment, or cure of diseases or injuries of man (per Section 351(a) of the Public Health Service Act (42 U.S.C. 262(a)). Further the term "biological agent" may include 1) "biomolecule", as used herein, encompassing a biologically active peptide, protein, carbohydrate, vitamin, lipid, or nucleic acid produced by and purified from naturally occurring or recombinant organisms, antibodies, tissues or cell lines or synthetic analogs of such molecules; 2) "genetic material" as used herein, encompassing nucleic acid (either deoxyribonucleic acid (DNA) or ribonucleic acid (RNA), genetic element, gene, factor, allele, operon, structural gene, regulator gene, operator gene, gene complement, genome, genetic code, codon, anticodon, messenger RNA (mRNA), transfer RNA (tRNA), ribosomal extrachromosomal genetic element, plasmagene, plasmid, transposon, gene mutation, gene sequence, exon, intron, and, 3) "processed biologics", as used herein, such as cells, tissues or organs that have undergone manipulation. The therapeutic agent may also include vitamin or mineral substances or other natural elements.

For devices placed in the vascular system, e.g., a stent, the amount of the therapeutic agent is preferably sufficient to inhibit restenosis or thrombosis or to affect some other state of the stented tissue, for instance, heal a vulnerable plaque, and/or prevent rupture or stimulate endothelialization. The agent(s) may be selected from the group consisting of antiproliferative agents, anti-inflammatory, anti-matrix metalloproteinase, and lipid lowering, cholesterol modifying, anti-thrombotic and antiplatelet agents, in accordance with preferred embodiments of the present invention. In some preferred embodiments of the stent, the therapeutic agent is contained within the stent as the agent is blended with the polymer or admixed by other means known to those skilled in the art. In other preferred embodiments of the stent, the therapeutic agent is delivered from a polymer coating on the stent surface. In another preferred variation the therapeutic agent is delivered by means of no polymer coating. In other preferred embodiments of the stent, the therapeutic agent is delivered from at least one region or one surface of the stent. The therapeutic may be chemically bonded to the polymer or carrier used for delivery of the therapeutic of at least one portion of the stent and/or the therapeutic may be chemically bonded to the polymer that comprises at least one portion of the stent body. In one preferred embodiment, more than one therapeutic agent may be delivered.

In certain embodiments, any of the aforementioned devices described herein can be adapted for use as a therapeutic delivery device (in addition to any other functionality thereof). Controlled therapeutic delivery systems may be prepared, in which a therapeutic agent, such as a biologically or pharmaceutically active and/or passive agent, is physically embedded or dispersed within a polymeric matrix or physically admixed with a polymer described herein. Controlled therapeutic agent delivery systems may also be prepared by direct application of the therapeutic agent to the surface of an implantable medical device such as a bioresorbable stent device (comprised of at least one of the polymers described herein) without the use of these polymers as a coating, or by use of other polymers or substances for the coating.

Therapeutic agent delivery compounds may also be formed by physically blending the therapeutic agent to be delivered with the polymers described herein using conventional techniques well-known to those of ordinary skill in the art. For this therapeutic agent delivery embodiment, it is not essential that the polymer have pendent groups for covalent attachment of the therapeutic agent.

The polymer compositions described herein containing therapeutic agents, regardless of whether they are in the form of polymer conjugates or physical admixtures of polymer and therapeutic agent, are suitable for applications where localized delivery is desired, as well as in situations where a systemic delivery is desired. The polymer conjugates and physical admixtures may be implanted in the body of a patient in need thereof, by procedures that are essentially conventional and well-known to those of ordinary skill in the art.

The polyarylates can also be formed into drug delivery implants that degrade to release pharmacologically or biologically active agents within a predictable controlled release time. Such controlled drug delivery systems can be prepared by incorporating the active agents into the polymer chains as pendant side chains or by cross linking the pendant side chains to form a polymeric matrix into which the active agents are physically embedded or dispersed. Controlled drug delivery system implants can also be formed by physically admixing the polyarylates with a biologically or pharmacologically active agent. The foregoing procedures are essentially conventional and well-known to those of ordinary skill in the art.

For controlled drug delivery systems in which a biologically or pharmacologically active agent is physically embedded or dispersed into a polymeric matrix or physically admixed with a polyarylate, suitable biologically or pharmacologically active agents include in principle any active agent that has to be repeatedly administered over prolonged periods of time.

An advantage of using the radiopaque, bioresorbable polymers described herein in therapeutic agent delivery applications is the ease of monitoring release of a therapeutic agent and the presence of the implantable therapeutic delivery system. Because the radiopacity of the polymeric matrix is due to covalently attached halogen substituents, the level of radiopacity is directly related to the residual amount of the degrading therapeutic agent delivery matrix still present at the implant site at any given time after implantation. In preferred embodiments the rate of therapeutic release from the degrading therapeutic delivery system will be correlated with the rate of polymer resorption. In such preferred embodiments, the straight-forward, quantitative measurement of the residual degree of radio-opacity will provide the attending physician with a way to monitor the level of therapeutic release from the implanted therapeutic delivery system.

The following non-limiting examples set forth herein below illustrate certain aspects of the invention. All parts and percentages are by mole percent unless otherwise noted and all temperatures are in degrees Celsius unless otherwise indicated. All solvents were HPLC grade and all other reagents were of analytical grade and used as received, unless otherwise indicated.

EXAMPLES

All the reagents were purchased in pure form and were used as received. Solvents were of "HPLC" or "ACS reagent" grade.

Generally, the diphenolic monomers were prepared by Fisher-esterification of tyrosol with phenolic acids such as desaminotyrosine, 3,5-diiododesaminotyrosine or dicarboxylic acids (0.5 equivalents) by refluxing with catalytic amount of 4-toulenesulfonic acid in chloroform or 1,2-dichloroethane as the solvent. A modified Dean Stark trap was used to remove the water formed. The diphenolic monomers in the pure form or as appropriate mixtures were polymerized to the corresponding polycarbonates using triphosgene. The polymers were compression molded into films. The films were tested for mechanical properties and they generally showed high modulus, tensile strength, and elongation at break. Further details are provided below.

Example 1. Synthesis of 4-Hydroxyphenethyl 3-(4-Hydroxyphenyl)Propanoate (DTy)

Into a 500 mL round bottomed flask fitted with an overhead stirrer, and a modified Dean-stark trap for solvents heavier than water were added 10 g (72 mmol) of tyrosol, 13 g (78 mmol) of desaminotyrosine (DAT), 0.65 g (3.4 mmol) of 4-toluenesulfonic acid monohydrate, and 200 mL of 1,2-dichloroethane (DCE). A water-cooled reflux condenser was placed on top of the modified Dean-stark trap and the contents of the flask were heated to reflux while being stirred. The reaction was continued until approximately 1.4 mL of water collected in the modified Dean-stark trap above the DCE and the water collection essentially stopped (about 4 hours of reflux). The reaction mixture was cooled to room temperature when the crude product precipitated as off-white crystalline solid, which was dissolved in 100 mL of ethyl acetate and washed twice with 100 mL portions of 5% sodium bicarbonate solution. After drying over magnesium sulfate the organic layer was concentrated and precipitated with hexane. The resulting white crystalline solid was collected by filtration and dried in a vacuum oven at 25° C. The product was characterized by elemental analysis, HPLC, and $^1$H NMR.

Using a similar procedure, 4-hydroxyphenethyl 4-hydroxyphenyl acetate (HPTy, compound of Formula (V) where $L^1$=$L^4$=bond, m=2, n=1, y1=y2=0) was prepared by substituting 4-hydroxyphenyl acetic acid for desaminotyrosine. The product was characterized by hplc and $^1$H NMR.

Using a similar procedure, 4-hydroxyphenethyl 2-(4-hydroxyphenoxy) acetate (compound of Formula (V) where $L^1$=bond, $L^4$=—O—, m=2, n=1, y1=y2=0) is prepared by substituting 2-(4-hydroxyphenoxy)acetic acid for desaminotyrosine. Similar results are obtained.

Using similar procedures, a monomer having the structure below (compound of Formula (VI) where Z=—NH—C(O)—CH$_3$, X$^1$=I, y1=2, y2=0) is prepared by reacting N-acetyltyrosine with diiodotyrosol using a solvent or mixture of solvents in which the N-acetyl tyrosine is more soluble than in 1,2-dichloroethane. Similar results are obtained.

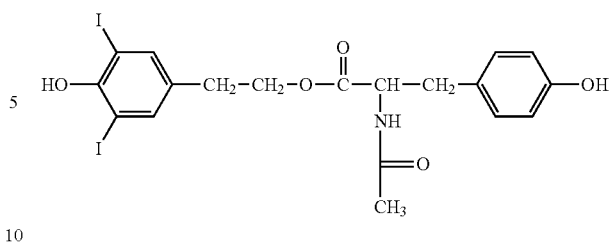

Using similar procedures, a monomer having the structure below (compound of Formula (VI) where Z=—NH—C(O)—CH$_3$, y1=y2=0) is prepared by reacting N-acetyltyrosine with tyrosol using a solvent or mixture of solvents in which N-acetyl tyrosine is more soluble than in 1,2-dichloroethane. Similar results are obtained.

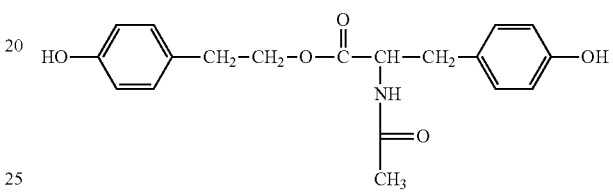

Example 2. Synthesis of 4-hydroxyphenethyl 3-(4-hydroxy-3,5-diiodophenyl)-propanoate (I$_2$DTy)

Into a 500 mL round bottomed flask fitted with an overhead stirrer, and a modified Dean-stark trap for solvents heavier than water were added 34.5 g (0.250 mol) of tyrosol, 102 g (0.244 mol) of 3-(4-hydroxy-3,5-diiodophenyl)propanoic acid (I$_2$DAT), 4.76 g (0.025 mol) of 4-toluenesulfonic acid monohydrate, and 500 mL of DCE. A water-cooled reflux condenser was placed on top of the modified Dean-stark trap and the contents of the flask were heated to reflux while being stirred. The reaction was continued until approximately 4.8 mL of water collected in the modified Dean-stark trap above the DCE and the water collection essentially stopped. The reaction mixture was allowed to cool to room temperature when the crude product precipitated as off-white crystals which was dried and then dissolved in 350 mL of tetrahydrofuran (thf). To this solution was added while stirring 1 L of 5% aqueous sodium bicarbonate solution stirred for 10 m and then allowed stand when the layers separated. The top layer was removed and discarded. The bottom layer was washed with two 500 mL portions of 5% aqueous sodium bicarbonate solution. I$_2$DTy precipitated as white crystalline solid. This was isolated by filtration and washed with 3×50 mL of deionized water. The product was dried under vacuum at 40° C. for 24 h and characterized by elemental analysis, HPLC, and $^1$H NMR.

Using similar procedures, 4-hydroxyphenethyl 2-(4-hydroxy-3,5-diiodophenyl)acetate (I$_2$HPTy) was prepared by substituting 2-(4-hydroxy-3-5-diiodophenyl)acetic acid for I$_2$DAT, and characterized by hplc and $^1$H NMR.

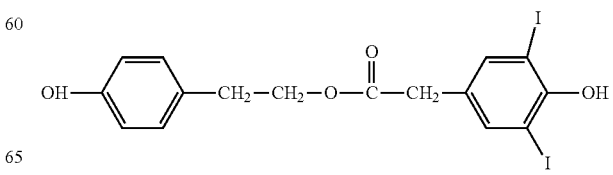

4-hydroxyphenethyl 2-(4-hydroxy-3,5-diiodophenyl)acetate

Using similar procedures, 4-hydroxy-3,5-diiodophenethyl 3-(4-hydroxy-3,5-diiodophenyl)propionate is prepared by substituting 4-(2-hydroxyethyl)-2,6-diiodophenol for tyrosol.

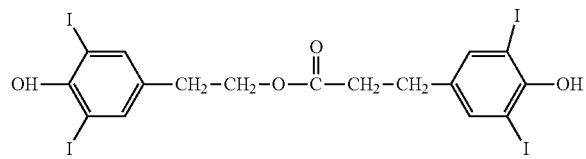 [SMILES: O=C(CCc1cc(I)c(O)c(I)c1)OCCc1cc(I)c(O)c(I)c1]

4-hydroxy-3,5-diiodophenethyl 3-(4-hydroxy-3,5-diiodophenyl)propionate

Example 3. Synthesis of Dityrosyl Succinate

Into a 500 mL round bottomed flask fitted with an overhead stirrer, and a modified Dean-stark trap for solvents heavier than water were added 25.0 g (0.181 mol) of tyrosol, 9.56 g (0.088 mol) of succinic acid, 3.44 g (18.1 mmol) of 4-toluenesulfonic acid monohydrate, and 200 mL of DCE. A water-cooled reflux condenser was attached to the top of the modified Dean-stark trap and the contents of the flask were heated to reflux while being stirred. The reaction was continued until approximately 3.2 mL of water collected in the modified Dean-stark trap above the DCE and the water collection essentially stopped. The reaction mixture was allowed to cool to room temperature while stirring was continued. The product that precipitated was isolated by filtration and washed with 2×50 mL of DCE. $^1$H NMR showed residual PTSA and tyrosol. For purification the solid was stirred with 150 mL of aqueous 5% NaHCO$_3$ for 3 h using overhead stirrer. The product was isolated by filtration and washed with 3×50 mL of DI water and then dried in the vacuum oven for 24 h at 50° C. The product was dried under vacuum at 40° C. for 24 h and characterized by elemental analysis, HPLC, and $^1$H NMR spectroscopy.

Example 4. Synthesis of Dityrosyl Oxalate

Into a 500 mL round bottomed flask fitted with an overhead stirrer, and a modified Dean-stark trap for solvents heavier than water were added 25.0 g (0.181 mol) of tyrosol, 8.00 g (0.088 mol) of Oxalic acid, 3.44 g (18.1 mmol) of 4-toluenesulfonic acid monohydrate, and 200 mL of 1,2-DCE. A water-cooled reflux condenser was attached to the top of the modified Dean-stark trap and the contents of the flask were heated to reflux while being stirred. The reaction was continued until approximately 3.2 mL of water collected in the modified Dean-stark trap above the DCE and the water collection essentially stopped. The reaction mixture was allowed to cool to room temperature while stirring was continued. The product that precipitated was isolated by filtration and washed with 2×50 mL of DCE. For purification the solid was stirred with 150 mL of aqueous 5% NaHCO$_3$ for 3 h using overhead stirrer. The product was isolated by filtration and washed with 3×50 mL of DI water and then dried in the vacuum oven for 24 h at 50° C. The product was dried under vacuum at 40° C. for 24 h and characterized by elemental analysis, HPLC, and $^1$H NMR spectroscopy.

Example 5. Polymerization of DTy and HPTy using Triphosgene

In a 500 mL 3-necked round-bottomed flask equipped with a mechanical stirrer, and a liquid addition device were placed 8.0 g (0.035 mol) of DTy, 9.5 g (0.12 mol) of pyridine, 70 mL of dichloromethane (DCM) and stirred for 15 min to get a clear solution. Triphosgene (3.6 g, 0.036 mol) was dissolved in 15 mL of DCM and the solution was introduced into the reaction flask over 2-3 hours. After the addition was complete, 100 mL of water was added to the reaction mixture and stirred for 5 min. After allowing the layers to separate, the top aqueous layer was removed and discarded. The washing as above was repeated with two additional 100 mL portions of DI water. The reaction mixture was then precipitated with 120 mL of IPA. The resulting gel was ground twice with 150 mL portions of IPA in 1 L laboratory blender. The product was isolated by vacuum filtration and dried in a vacuum oven at 80° C. for 24 h. The polymer had a HPSEC polystyrene equivalent molecular weight of 160 Kda (THF as mobile phase). The polymer was semi-crystalline with a Tg of 51° C. and a Tm of 181° C. On compression molding at 220° C., it gave films which were transparent on rapid cooling and translucent when cooled slowly. The tensile modulus, tensile stress at yield, and elongation at break were respectively 210 ksi, 5 ksi and 500%. Using similar procedures, HPTy (obtained in accordance with Example 1) was polymerized to obtain poly (HPTy carbonate) with an HPSEC polystyrene equivalent Mw of 140 Kda and a Tg of 55° C.

Example 6. Polymerization of I$_2$DTy and I$_2$HPTy using Triphosgene

In a 500 mL 3-necked round-bottomed flask equipped with a mechanical stirrer, and a controlled liquid addition device were placed 25 g (0.046 mol) of I$_2$DTy, 14.3 g (0.181 mol) of pyridine, 200 mL of DCM and stirred for 15 min to get a clear solution. Triphosgene (5.1 g, 0.052 mol of phosgene) was dissolved in 20 mL of DCM and the solution was to the reaction flask over 2-3 hours. After the addition was complete, 250 mL of water was added to the reaction mixture and stirred for 5 min. After allowing the layers to separate, the top aqueous layer was removed and discarded. The washing was repeated with two additional 250 mL portions of DI water. The reaction mixture was then precipitated with 350 mL of IPA. The resulting gel was ground twice with 200 mL portions of IPA in a 1 L laboratory blender. The product was isolated by vacuum filtration and dried in a vacuum oven at 80° C. for 24 h. The polymer had a HPSEC polystyrene equivalent molecular weight of 176 Kda (THF as mobile phase) and glass transition temperature (Tg) of 112° C. Compression molding at 205° C. gave a uniform transparent film which gave tensile modulus, tensile stress at yield, and elongation at break respectively of 230 ksi, 9.2 ksi and 220%. Using similar procedures, I$_2$HPTy (obtained in accordance with Example 2) was polymerized to obtain poly(I$_2$HPTy carbonate).

Example 7. Preparation of Poly(I$_2$DTy-co-10 weight % PEG2K carbonate)

In a 250 mL 3-necked round-bottomed flask equipped with a mechanical stirrer, and a liquid addition device were placed 9.0 g (0.017 mol) of I$_2$DTy, 1.01 g of PEG2000, 5.4 g (0.068 mol) of pyridine, and 65 mL of DCM and stirred for 15 min to get a clear solution. Triphosgene (2.0 g, 0.020 mol of phosgene) was dissolved in 10 mL of DCM and the solution was introduced into the reaction flask over 2-3 hours. After the addition was complete, 100 mL of water was added to the reaction mixture and stirred for 5 min. After allowing the layers to separate, the top aqueous layer was removed and discarded. The washing was repeated with two additional 100 mL portions of DI water. The reaction mixture was then precipitated with 100 mL of IPA. The resulting gel was ground twice with 150 mL portions of IPA in 1 L laboratory blender. The product was isolated by vacuum filtration and dried in a vacuum oven at 50° C. The polymer had a HPSEC polystyrene equivalent molecular weight of 250 Kda (THF as mobile phase) and glass transition temperature (Tg) of 64° C. and gave a clear film on compression molding at 205° C. The tensile stress at yield, the tensile modulus and elongation at break respectively were 7.1 ksi, 235 ksi and 350%.

Example 8. Preparation of Poly($I_2$DTy-co-5 weight % PEG2K Carbonate)

In a 250 mL 3-necked round-bottomed flask equipped with a mechanical stirrer, and a liquid addition device were placed 10 g (0.019 mol) of $I_2$DTy, 0.535 g of PEG2000, 5.9 ml (0.073 mol) of pyridine, and 62 mL of DCM and stirred for 15 min to get a clear solution. Triphosgene (2.1 g, 0.021 mol of phosgene) was dissolved in 10 mL of DCM and the solution was introduced into the reaction flask over 2-3 hours. After the addition was complete, 100 mL of water was added to the reaction mixture and stirred for 5 min. After allowing the layers to separate, the top aqueous layer was removed and discarded. The washing was repeated with two additional 100 mL portions of DI water. The reaction mixture was then precipitated with 100 mL of IPA. The resulting gel was ground twice with 150 mL portions of IPA in 1 L laboratory blender. The product was isolated by vacuum filtration and dried in a vacuum oven at 50° C. The polymer had a HPSEC polystyrene equivalent molecular weight of 200 Kda (THF as mobile phase) and glass transition temperature (Tg) of 84° C. Compression molding at 205° C. gave a uniform transparent film which gave tensile modulus, tensile stress at yield, and elongation at break respectively of 232 ksi, 8.2 ksi and 70%.

Example 9. Preparation of Poly($I_2$DTy-co-10 weight % PTMC5K carbonate)

In a 250 mL 3-necked round-bottomed flask equipped with a mechanical stirrer, and a liquid addition device were placed 9.0 g (0.017 mol) of $I_2$DTy, 1.00 g of poly(trimethylene carbonate) of Mn 5000 (PTMC5K), 5.5 ml (0.068 mol) of pyridine, and 65 mL of DCM and stirred for 15 min to get a clear solution. Triphosgene (1.9 g, 0.019 mol of phosgene) was dissolved in 10 mL of DCM and the solution was introduced into the reaction flask over 2-3 hours. After the addition was complete, 100 mL of water was added to the reaction mixture and stirred for 5 min. After allowing the layers to separate, the top aqueous layer was removed and discarded. The washing was repeated with two additional 100 mL portions of DI water. The reaction mixture was then precipitated with 100 mL of IPA. The resulting gel was ground twice with 150 mL portions of IPA in 1 L laboratory blender. The product was isolated by vacuum filtration and dried in a vacuum oven at 50° C. The polymer had a HPSEC polystyrene equivalent molecular weight of 250 Kda (THF as mobile phase) and glass transition temperature (Tg) of 101° C. Compression molding at 205° C. gave a uniform transparent film which gave tensile modulus, tensile stress at yield, and elongation at break respectively of 201 ksi, 7.4 ksi and 120%.

Example 10. Preparation of Poly($I_2$DTy-co-5 weight % PTMC5K carbonate)

In a 250 mL 3-necked round-bottomed flask equipped with a mechanical stirrer, and a liquid addition device were placed 10 g (0.019 mol) of $I_2$DTy, 0.53 g of PTMC5K, 5.9 ml (0.073 mol) of pyridine, and 65 mL of DCM and stirred for 15 min to get a clear solution. Triphosgene (2.1 g, 0.021 mol of phosgene) was dissolved in 10 mL of DCM and the solution was introduced into the reaction flask over 2-3 hours. After the addition was complete, 100 mL of water was added to the reaction mixture and stirred for 5 min. After allowing the layers to separate, the top aqueous layer was removed and discarded. The washing was repeated with two additional 100 mL portions of DI water. The reaction mixture was then precipitated with 100 mL of IPA. The resulting gel was ground twice with 150 mL portions of IPA in 1 L laboratory blender. The product was isolated by vacuum filtration and dried in a vacuum oven at 50° C. The polymer had a HPSEC polystyrene equivalent molecular weight of 225 Kda (THF as mobile phase) and glass transition temperature (Tg) of 106° C. Compression molding at 205° C. gave a uniform transparent film which gave tensile modulus, tensile stress at yield, and elongation at break respectively of 266 ksi, 8.4 ksi and 185%.

Example 11. Synthesis of di-ester of 1,3-propanediol with $I_2$DAT (PrD-di $I_2$DAT)

Into a 500 mL round-bottomed flask equipped with an overhead stirrer, a Dean-Stark trap and a thermometer were added 3.04 g (0.040 mol) of 1,3-propanediol, 33.8 g (0.081 mol) of 3,5-diiododesaminotyrosyl tyrosine ethyl ester ($I_2$DAT), 0.76 g (4.0 mmol) of p-toluenesulfonic acid, and 200 mL of 1,2-dichloroethane. The flask was heated using a heating mantle, while stirring with the overhead stirrer so that 1,2-dichloroethane and water distilled over into the Dean-Stark trap. The heating continued until the water collection stopped (about 1.45 mL of water was collected). The reaction mixture was allowed to cool to 50° C. and then evaporated to dryness. To the residue 175 mL of acetonitrile was added and stirred at room temperature for 4 h. The crystalline solid that separated was isolated by filtration and washed with acetonitrile. The Off-white crude product was collected and dried.

The crude PrD-di $I_2$DAT obtained above (98% pure by HPLC) was stirred with 175 mL of acetonitrile for 4 h using a overhead stirrer at 200 rpm. The product precipitated as almost colorless powder, which showed a purity of ca 98-99% by HPLC. For further purification the product was dissolved in acetonitrile (10 mL/g) and stirred with Norit (10 mg of Norit/g of product). The hot solution was filtered to remove Norit and then cooled in ice-water bath for recrystallization when colorless powder was obtained (purity >99.5% by HPLC). The product was dried in vacuum oven at 40° C. The product had a melting point of 88° C. (by DSC) and the elemental analysis and $^1$H NMR spectrum were in agreement with the structure. Further purification can be achieved by column chromatography on silica gel.

Example 12. Preparation of Poly(PrD-di $I_2$DAT-co-10 Weight % Tyrosol Carbonate)

In a 1 L 3-necked round-bottomed flask equipped with a mechanical stirrer, and a liquid addition device were placed 25 g (0.029 mol) of PrD-di I$_2$DAT, 2.78 g (0.020 mol) of tyrosol, 15.4 ml (0.19 mol) of pyridine, and 170 mL of DCM and stirred for 15 min to get a clear solution. Triphosgene (5.4 g, 0.055 mol of phosgene) was dissolved in 20 mL of DCM and the solution was introduced into the reaction flask over 2-3 hours. After the addition was complete, the 200 mL of water was added to the reaction mixture and stirred for 5 min. After allowing the layers to separate, the top aqueous layer was removed and discarded. The washing was repeated with two additional 200 mL portions of DI water. The reaction mixture was then precipitated with 300 mL of IPA. The resulting gel was ground twice with 200 mL portions of IPA in 1 L laboratory blender. The product was isolated by vacuum filtration and dried in a vacuum oven at 80° C. The polymer had a HPSEC polystyrene equivalent molecular weight of 200 Kda (THF as mobile phase) and glass transition temperature (Tg) of 90° C. $^1$H NMR spectrum of the polymer was in agreement with the structure. Compression molding at 205° C. gave a uniform transparent film which gave tensile modulus, tensile stress at yield (a), and elongation at break respectively of 260 ksi, 9.7 ksi and 220%. Using similar procedures copolymers with 5%, and 15% tyrosol were prepared as follows:

| % tyrosol | Tg, °C. | σ, ksi | Modulus, ksi | Elongation, % |
|---|---|---|---|---|
| 5 | 104 | 9.8 | 254 | 41 |
| 15 | 90 | 9.5 | 244 | 164 |

As will be understood by a person of ordinary skill in the art, since triphogene is added slowly into the mixture of the reactants PrD-di I$_2$DAT and tyrosol, the poly(PrD-di I$_2$DAT-co-tyrosol carbonate) product is composed of mainly polymer molecules having randomly-ordered PrD-di I$_2$DAT and tyrosol units connected through carbonate (—OC(O)O—) linkers. That is, two adjacent units could include PrD-di I$_2$DAT and PrD-di I$_2$DAT, PrD-di I$_2$DAT and tyrosol, or tyrosol and tyrosol. Given the unsymmetrical structure of tyrosol, it can be connected with a PrD-di I$_2$DAT unit using either "head" (i.e., "phenoxy" moiety) or "tail" (i.e., the "ethylenoxy" moiety). Any two adjacent units formed from tyrosol itself can be in any of the "head-head", "head-tail" or "tail-tail" arrangements. In this Example, without intending to be bound by theory, since the PrD-di I$_2$DAT was used in molar excess, the polymer molecules likely do not contain a large amount of long strings of "tyrosol-carbonate-tyrsol" units linked to each other. On the other hand, if there is a large excess of tyrosol relative to the PrD-di I$_2$DAT in the reaction mixture, tyrosol may have more opportunity to link with each other to give relatively long strings of such linkages.

Example 13. Poly(Tyrosol Carbonate)

In a 500 mL 3-necked round-bottomed flask equipped with a mechanical stirrer, and a liquid addition device were placed 10 g (0.073 mol) of tyrosol, 24 ml (0.298 mol) of pyridine, 200 mL of DCM and stirred for 15 min to get a clear solution. Triphosgene (7.7 g, 0.078 mol of phosgene) was dissolved in 25 mL of DCM and the solution was introduced into the reaction flask over 2-3 hours. After the addition was complete, 250 mL of water was added to the reaction mixture and stirred for 5 min. After allowing the layers to separate, the top aqueous layer was removed and discarded. The washing was repeated with two additional 250 mL portions of DI water. The reaction mixture was then precipitated with 300 mL of IPA. The resulting gel was ground twice with 200 mL portions of IPA in 1 L laboratory blender. The product was isolated by vacuum filtration and dried in a vacuum oven at 60° C. The polymer had a HPSEC polystyrene equivalent molecular weight of 126 Kda (THF as mobile phase) and glass transition temperature (Tg) of 58° C. Compression molding at 195° C. gave a uniform transparent film which gave tensile modulus, tensile stress at yield, and elongation at break respectively of 191 ksi, 5 ksi and 450%.

Example 14. Low Molecular Weight Poly(Tyrosol Carbonate)

In a 250 mL 3-necked round-bottomed flask equipped with a mechanical stirrer, and a liquid addition device were placed 10 g (0.073 mol) of tyrosol, 22 ml (0.277 mol) of pyridine, 60 mL of DCM and stirred for 15 min to get a clear solution. Triphosgene (7.0 g, 0.071 mol of phosgene) was dissolved in 25 mL of DCM and the solution was introduced into the reaction flask over 2-3 hours. After the addition was complete, the 100 mL of 0.2 M aqueous HCl was added to the reaction mixture and stirred for 5 min. After allowing the layers to separate, the top aqueous layer was removed and discarded. The washing was repeated with three additional 100 mL portions of 0.2 M aqueous HCl. The reaction mixture was then dried over anhydrous magnesium sulfate and then precipitated with 100 mL of hexane. The resulting viscous oil was stirred with 200 mL of fresh hexane until the product solidified into a white solid. The product was transferred to a glass dish dried in a vacuum oven at 60° C. The polymer had a HPSEC polystyrene equivalent Mw of 7500 da and Mn of 5700 da (THF as mobile phase) and glass transition temperature (Tg) of 48° C. A number of oligomers and polymers ranging in Mw from 750 da to 40,000 da were prepared using this method.

Example 15. Preparation of multi-block Poly(PrD-di I$_2$DAT-co-10 Weight % Tyrosol Carbonate)

In a 1 L 3-necked round-bottomed flask equipped with a mechanical stirrer, and a liquid addition device were placed 25 g (0.029 mol) of PrD-di I$_2$DAT, 2.78 g (0.49 mmol) of oligo(tyrosol carbonate) with Mn of 5700 da, 15.4 ml (0.19 mol) of pyridine, and 170 mL of DCM and stirred for 15 min to get a clear solution. Triphosgene (3.3 g, 0.055 0.034 mol of phosgene) was dissolved in 20 mL of DCM and the solution was introduced into the reaction flask over 2-3 hours. After the addition was complete, the reaction mixture was stirred for 15 min. To the viscous reaction mixture 200 mL of water was added and stirred for 5 min. After allowing the layers to separate, the top aqueous layer was removed and discarded. The washing was repeated with two additional 200 mL portions of DI water. The reaction mixture was then precipitated with 300 mL of IPA. The resulting gel was ground twice with 200 mL portions of IPA in 1 L laboratory blender. The product was isolated by vacuum filtration and dried in a vacuum oven at 80° C. The polymer had a HPSEC polystyrene equivalent molecular weight of 200 Kda (THF as mobile phase) and glass transition temperature (Tg) of 90° C. $^1$H NMR spectrum of the polymer was in agreement with the structure. The $^1$H NMR spectrum of this polymer was significantly different from the random copolymer obtained as in example 13, indicative of the blockiness of the tyrosol recurring units.

Example 16. Preparation of Poly(PrD-di I₂DAT-co-10 weight % DTy Carbonate)

In a 1 L 3-necked round-bottomed flask equipped with a mechanical stirrer, and a liquid addition device were placed 25 g (0.029 mol) of PrD-di I₂DAT, 2.78 g (0.010 mol) of DTy, 15.4 ml (0.19 mol) of pyridine, and 170 mL of DCM and stirred for 15 min to get a clear solution. Triphosgene (4.3 g, 0.044 mol of phosgene) was dissolved in 20 mL of DCM and the solution was introduced into the reaction flask over 2-3 hours. After the addition was complete, the 200 mL of water was added to the reaction mixture and stirred for 5 min. After allowing the layers to separate, the top aqueous layer was removed and discarded. The washing was repeated with two additional 200 mL portions of DI water. The reaction mixture was then precipitated with 300 mL of IPA. The resulting gel was ground twice with 200 mL portions of IPA in 1 L laboratory blender. The product was isolated by vacuum filtration and dried in a vacuum oven at 80° C. The polymer had a HPSEC polystyrene equivalent molecular weight of 200 Kda (THF as mobile phase) and glass transition temperature (Tg) of 95° C. ¹H NMR spectrum of the polymer was in agreement with the structure. Compression molding at 205° C. gave a uniform transparent film which gave tensile modulus, ultimate tensile stress, and elongation at break respectively of 280 ksi, 10 ksi and 200%.

Example 17. Preparation of Tyrosol or Analog-Based Alternating Polycarbonates Alternating polymers having regular sequences of tail-tail, head-head, and/or head-tail configurations are disclosed. These polymers are distinctly different from random polymers having no specific order of tail-tail, head-head, and/or head-tail configurations. Specifically, polycarbonates derived from tyrosol, have three types of carbonate bonds: aromatic-aromatic (also referred to as head-head), mixed aromatic-aliphatic (also referred to as head-tail), and aliphatic-aliphatic (also referred to as tail-tail) as shown below:

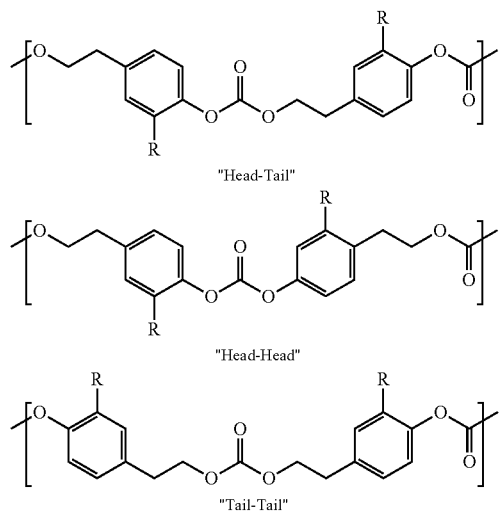

R = H (tyrosol) or OMe (homovanillyl alcohol)

Polymers having a random sequence of H-H, H-T, or T-T backbone linkages can have distinctly different properties from those having a regular sequence of backbone linkages. To create alternating polymers with a regular, alternating sequence of H-H and T-T bonds, the monomer was reacted with itself to form a dimer. Then, the dimer was subjected to a polymerization reaction. In this example, aliphatic dityrosol carbonate and aliphatic tyrosol chloroformate were used as monomers for polycarbonate synthesis. Aliphatic dityrosol carbonate introduces an enzymatic cleavage site due to the flexibility and steric accessibility of the aliphatic carbonate bond. The reaction steps are outlined below.

(A) Synthesis of Tyrosol Chloroformate

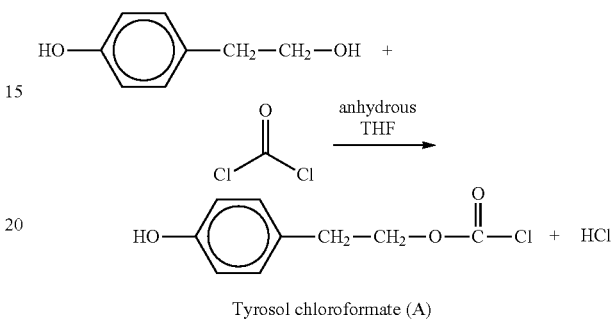

Tyrosol chloroformate (A)

Tyrosol was placed in a three-necked flask equipped with an overhead stirrer under inert atmosphere. Anhydrous tetrahydrofuran was added from a syringe and a solution was obtained while the mixture was stirred. The solution was constantly cooled with an ice/water bath. Triphosgene was dissolved in anhydrous tetrahydrofuran and added drop-wise to the reaction vessel. Aliphatic tyrosol chloroformate was obtained over the course of one hour. Most of the solvent was evaporated to prepare for the work-up. Methylene chloride was added to dissolve the residue and excess tyrosol was filtered off. The solution was cooled in an ice/water bath. Cooled deionized water was added to remove most of the HCl built up during the reaction. The two layers were separated and the organic phase was dried over magnesium sulfate. The solvent was evaporated, and after drying under vacuum aliphatic tyrosol chloroformate was obtained as an oil.

(B) Synthesis of Aliphatic Dityrosol Carbonate

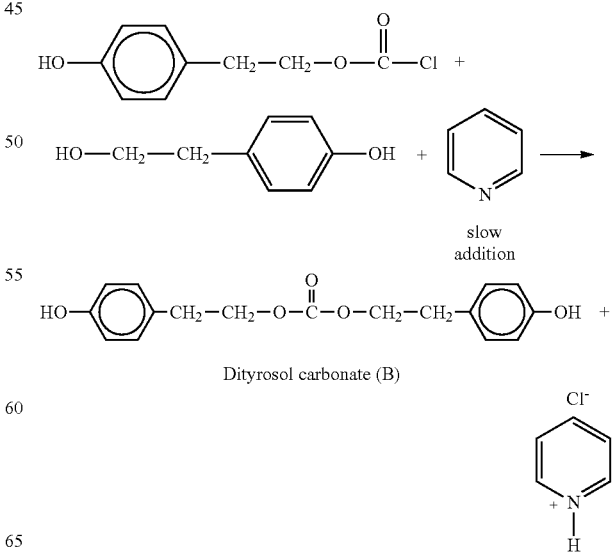

Dityrosol carbonate (B)

Aliphatic tyrosol chloroformate (A) and tyrosol were dissolved in anhydrous tetrahydrofuran under nitrogen atmosphere and cooled with an ice/water bath. One equivalent of pyridine was added drop-wise using a syringe pump over the course of twelve hours. Then the solvent was evaporated, and the residue dissolved in methylene chloride. The organic phase was washed 4 times with dilute HCl, 4 times with 5% (w/v) aqueous bicarbonate and twice with brine. The organic layer was dried over magnesium sulfate. After drying dityrosol carbonate was obtained as a white solid.

(C) Synthesis of Poly(Tyrosol Carbonate) with Alternating Carbonate Bond Sequence

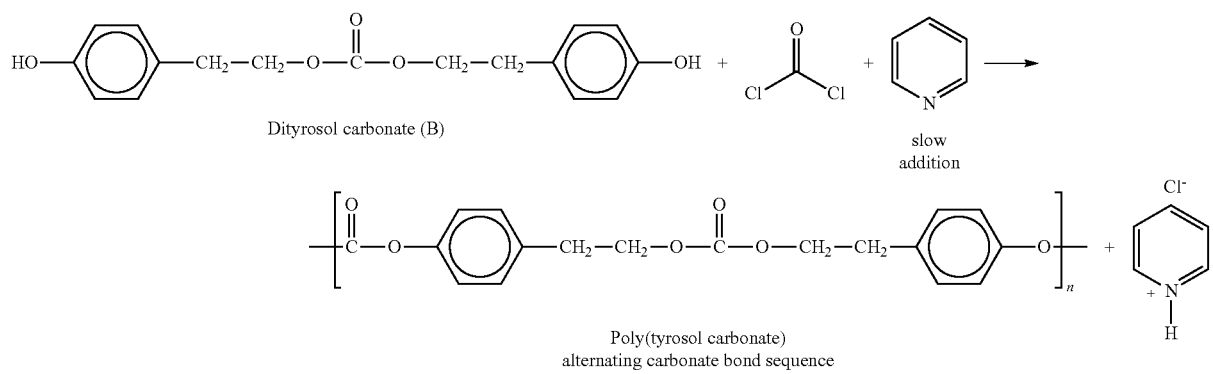

Aliphatic dityrosol carbonate is dissolved in methylene chloride under nitrogen atmosphere. Triphosgene is dissolved in methylene chloride and added drop-wise to the reaction mixture. After the triphosgene addition, pyridine is added drop-wise to the reaction mixture over the course of several hours. Poly(tyrosol carbonate) with alternating carbonate bond sequence is obtained by standard a workup procedure.

(D) Synthesis of Polytyrosol with Controlled Carbonate Bond Sequence

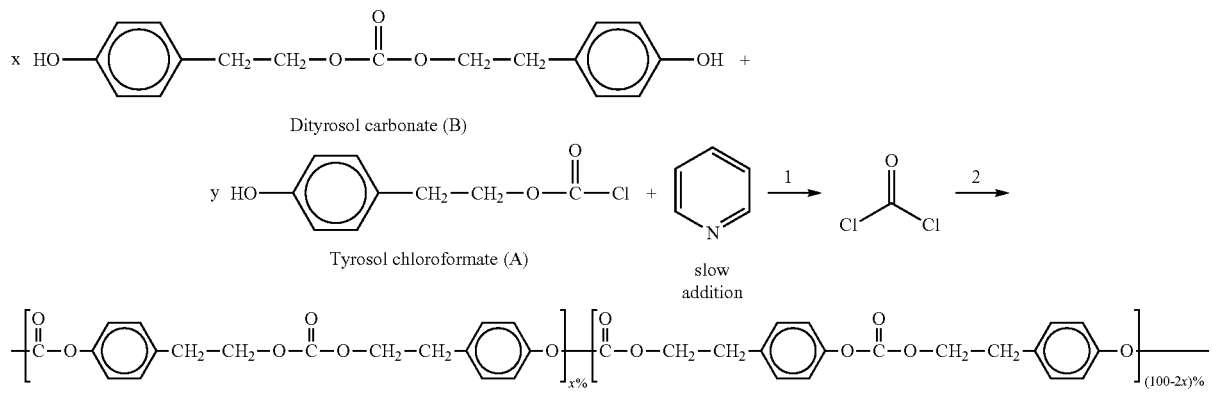

Dityrosol carbonate (x equivalents) and tyrosol carbonate (y equivalents) are dissolved in anhydrous tetrahydrofurane and cooled in dry ice/isopropanol bath. Pyridine is added drop-wise over the course of several hours in step 1. Then triphosgene dissolved in anhydrous tetrahydrofuran is added drop-wise into the reaction mixture. The poly(tyrosol carbonate) with controlled composition of carbonate bonds is obtained through a standard work-up procedure.

It will be understood by those of skill in the art that numerous and various modifications can be made without departing from the spirit of the present invention. Therefore, it should be clearly understood that the various embodiments of the present invention described herein are illustrative only and not intended to limit the scope of the present invention.

Example 18. Preparation of poly(PrDI$_2$DAT-co-9% tyrosol-co-1% PEG1K Carbonate)

In a 1 L 3-necked round-bottomed flask equipped with a mechanical stirrer, and a liquid addition device were placed 45 g (51 mmol) of PrD-di I$_2$DAT, 4.5 g (33 mol) of tyrosol, 0.5 g (0.50 mmol) of PEG1000, 25 g (320 mmol) of pyridine, and 305 mL of DCM and stirred for 15 min to get a clear solution. Triphosgene (8.6 g, 87 mmol of phosgene) was dissolved in 32 mL of DCM and the solution was introduced into the reaction flask over 2-3 hours. After the addition was complete, the reaction mixture was quenched with a mixture of 135 mL of THF and 15 mL of water. 350 mL of water was added to the reaction mixture and stirred for 5 min. After allowing the layers to separate, the top aqueous layer was removed and discarded. The washing was repeated with two additional 350 mL portions of DI water. The reaction mixture was then precipitated with 500 mL of acetone. The resulting gel was stirred with 500 mL of IPA when the gel broke up into fine particles. The particles were ground twice, isolated by filtration and dried in a vacuum oven at 80° C. The polymer had a Mw of 400 Kda and glass transition temperature (Tg) of 92° C. $^1$H NMR spectrum of the polymer was in agreement with the structure. Compression molding at 190° C. gave a uniform transparent film which gave tensile modulus, tensile stress at yield, and elongation at break of 240 ksi, 9.1 ksi, and 106% respectively.

Example 19. Preparation of poly(I$_2$DTy-co-10% Tyrosol Carbonate)

In a 1 L 3-necked round-bottomed flask equipped with a mechanical stirrer, and a liquid addition device were placed 45 g (0.084 mol) of I$_2$DTy, 5 g (0.036 mol) of tyrosol, 35.5 g (0.45 mol) of pyridine, and 300 mL of DCM and stirred for 15 min to get a clear solution. Triphosgene (12.3 g, 0.125 mol of phosgene) was dissolved in 32 mL of DCM and the solution was introduced into the reaction flask over 2-3 hours. After the addition was complete, the reaction mixture was quenched with a mixture of 135 mL of THF and 15 mL of water. 350 mL of water was added to the reaction mixture and stirred for 5 min. After allowing the layers to separate, the top aqueous layer was removed and discarded. The washing was repeated with two additional 350 mL portions of DI water. The reaction mixture was then precipitated with 600 mL of IPA. The resulting gel was ground twice in a 4 L high speed blender. The precipitate obtained was isolated by filtration and dried in a vacuum oven at 80° C. The polymer had a Mw of 318 Kda and a glass transition temperature (Tg) of 100° C. $^1$H NMR spectrum of the polymer was in agreement with the structure. Compression molding at 190° C. gave a uniform transparent film. Using similar procedures a copolymer with 15% tyrosol was prepared. The properties of the polymers are set forth below:

| % tyrosol | Tg, ° C. | σ, ksi | Modulus, ksi | Elongation, % |
|---|---|---|---|---|
| 10 | 100 | 8.7 | 234 | 239 |
| 15 | 82 | 9.0 | 240 | 217 |

Example 20. Preparation of PLLAdiol Using Ethylene Glycol as Initiator (EGPLLAD7K)

Into a 250 mL round bottomed flask were transferred 1.29 g (0.02 mol) of ethylene glycol, 1.44 tg (3.6 mmol) of Sn(II)octoate and 144.1 g (1.0 mol) of L-lactide. A large egg-shaped stir bar was introduced into the flask. The flask was maintained under a positive pressure of nitrogen and then immersed into an oil bath maintained at 110° C. and after heating for 1 h the lactide melted. The temperature was raised to 140° C. and heated with stirring for 4 h. The flask was then removed from the oil bath and allowed to cool to room temperature. To the flask 350 mL of DCM was added and stirred overnight to dissolve the polymer. The polymer solution was slowly added to 1 L of heptane with stirring. The polymer precipitated as white crystalline powder which was isolated by filtration. The precipitate was washed with 250 mL of acetonitrile to remove any unreacted lactide. The product was dried in a vacuum oven at 40° C. for 24 h. DSC showed a Tg of 47° C. and melting points at 134° C. (5 J/g) and 148° C. (15.5 J/g). PrDPLLAD7K was similarly prepared using 1,3-propanediol as the initiator instead of ethylene glycol.

Example 21. Preparation of poly(PrD-di I$_2$DAT-co-50% EGPLLAD7K Carbonate)

In a 1 L 3-necked round-bottomed flask equipped with a mechanical stirrer, and a liquid addition device were placed 30 g (0.034 mol) of PrD-di I$_2$DAT, 30 g (0.004 mol) of EGPLLAD7K, 11.4 g (0.145 mol) of pyridine, and 360 mL of chloroform and stirred for 15 min to get a clear solution (the solution was slightly cloudy). Triphosgene (3.96 g, 0.04 mol of phosgene) was dissolved in 12 mL of chloroform and the solution was introduced into the reaction flask over 2-3 hours. After the addition was complete, the reaction mixture was quenched with a mixture of 135 mL of THF and 15 mL of water. 350 mL of water was added to the reaction mixture and stirred for 5 min. After allowing the layers to separate, the top aqueous layer was removed and discarded. The washing was repeated with two additional 350 mL portions of DI water. The reaction mixture was then precipitated with 700 mL of IPA. The resulting gel was ground with 550 mL twice in a 4 L blender. The product was isolated by filtration and dried in a vacuum oven at 80° C. $^1$H NMR spectrum of the polymer was in agreement with the structure. Compression molding at 190° C. of the obtained 50% EGPLLAD polymer gave a uniform transparent film.

Using similar procedures, copolymers containing 20% and 65% EGPLLAD were also prepared. The physical properties of the three polymer samples are set forth below. Other polymers having different physical properties can be prepared by routine experimentation informed by the guidance provided herein, e.g., by appropriate selection of comonomer content, polymer molecular weight and film preparation procedures.

| % EGPLLAD | Tg, ° C. | σ, ksi | Modulus, ksi | Elongation, % |
|---|---|---|---|---|
| 20 | 60 and 110 | 9.4 | 262 | 6 |
| 50 | Tg = 61<br>Tm = 150 | 8.0 | 274 | 162 |
| 65 | Tg = 62<br>Tm = 146 | 7.0 | 295 | 5 |

Example 22. Preparation of poly(I$_2$DTy-co-50% EGPLLAD7K Carbonate)

In a 1 L 3-necked round-bottomed flask equipped with a mechanical stirrer, and a liquid addition device were placed 25 g (0.046 mol) of I$_2$DTy, 25 g (0.004 mol) of EGPLLAD, 14.8 g (0.19 mol) of pyridine, and 305 mL of DCM and stirred for 15 min to get a clear solution. Triphosgene (5.19 g, 0.053 mol of phosgene) was dissolved in 15 mL of DCM and the solution was introduced into the reaction flask over 2-3 hours. After the addition was complete, the reaction mixture was quenched with a mixture of 135 mL of THF and 15 mL of water. 350 mL of water was added to the reaction mixture and stirred for 5 min. After allowing the layers to separate, the top aqueous layer was removed and discarded. The washing was repeated with two additional 350 mL portions of DI water. The reaction mixture was then precipitated with 600 mL of IPA. The resulting gel was ground twice in a 4 L high speed blender. The precipitate obtained was isolated by filtration and dried in a vacuum oven at 80° C. The polymer had a glass transition temperature (Tg) of 100° C. $^1$H NMR spectrum of the polymer was in agreement with the structure. Compression molding at 190° C. gave a uniform transparent film. Copolymers containing 45% and 60% of EGPLLAD were also prepared using similar procedures and characterized. The properties of the polymers are listed in the table below. Using similar procedures copolymers containing I$_2$DTE and polyglycolide-diols (PGAD) can be prepared by replacing PLLAD with PGAD in the above polymerization.

| % EGPLLAD | Tg, °C | σ, ksi | Modulus, ksi | Elongation, % |
|---|---|---|---|---|
| 45 | 62 and 106 | 8.2 | 275 | 17 |
| 50 | 62 and 106 | 8.0 | 247 | 106 |
| 60 | 60 | 7.9 | 257 | 188 |

Example 23. Preparation of poly($I_2$DTy-co-50% DTy Carbonate)

In a 1 L 3-necked round-bottomed flask equipped with a mechanical stirrer, and a liquid addition device were placed 25 g (0.046 mol) of $I_2$DTy, 25 g (0.087 mol) of DTy, 43 g (0.55 mol) of pyridine, and 305 mL of DCM and stirred for 15 min to get a clear solution. Triphosgene (14.2 g, 0.143 mol of phosgene) was dissolved in 43 mL of DCM and the solution was introduced into the reaction flask over 2-3 hours. After the addition was complete, the reaction mixture was quenched with a mixture of 135 mL of THF and 15 mL of water. 350 mL of water was added to the reaction mixture and stirred for 5 min. After allowing the layers to separate, the top aqueous layer was removed and discarded. The washing was repeated with two additional 350 mL portions of DI water. The reaction mixture was then precipitated with 600 mL of IPA. The resulting gel was ground twice in a 4 L high speed blender. The precipitate obtained was isolated by filtration and dried in a vacuum oven at 80° C. The polymer had a glass transition temperature (Tg) of 68° C. Compression molding at 170° C. gave a uniform transparent film which gave tensile modulus, tensile stress at yield, and elongation at break respectively of 195 ksi, 4.3 ksi, and 473%. Using similar procedure poly($I_2$DTy-co-20% DTy carbonate was prepared.

Example 24. Synthesis of (4-(2-hydroxyethyl) 2,6,-diiodophenol)

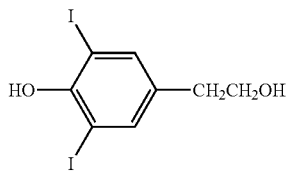

Iodination of tyrosol was carried out by adding 200 mL of $KICl_2$ solution (2M) to 27.6 g (0.2 mol) of tyrosol in 140 mL of 95% ethanol and stirring the resulting solution for 1 h. When treated with 400 mL of water, an oil separated which was stirred with 100 mL of 2% sodium thiosulfate solution for 2 h. The brown solid obtained was dissolved in ethanol and treated with charcoal and filtered. The pure diiodotyrosol (4-(2-hydroxyethyl) 2,6,-diiodophenol) was obtained in 65% yield and was characterized by hplc and NMR.

Example 25. Synthesis of 4-hydroxyphenethyl 3-(4-(4-hydroxyphenoxy)phenyl)-propanoate

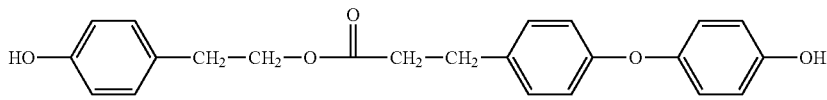

Into a 500 mL round bottomed flask fitted with an overhead stirrer, and a modified Dean-stark trap for solvents heavier than water are added 10 g (72 mmol) of tyrosol, 30 g (78 mmol) of desaminothyronine, 0.65 g (3.4 mmol) of 4-toluenesulfonic acid monohydrate, and 200 mL of 1,2-dichloroethane (DCE). A water-cooled reflux condenser is placed on top of the modified Dean-stark trap and the contents of the flask are heated to reflux while being stirred. The reaction is continued until approximately 1.4 mL of water collected in the modified Dean-stark trap above the DCE and the water collection essentially stopps (about 4 hours of reflux). The reaction mixture is cooled to room temperature and the crude product is dissolved in 100 mL of ethyl acetate and washed twice with 100 mL portions of 5% sodium bicarbonate solution. After drying over magnesium sulfate the organic layer is concentrated and precipitated with hexane. The resulting white crystalline solid is collected by filtration and dried in a vacuum oven at 25° C. The product is characterized by elemental analysis, hplc, and $^1$H NMR.

It will be understood by those skilled in the art that numerous and various modifications can be made without departing from the spirit of the present invention. Therefore, the various embodiments and examples of the present invention described herein are illustrative only and not intended to limit the scope of the present invention.

What is claimed is:
1. A diphenol compound of formula:

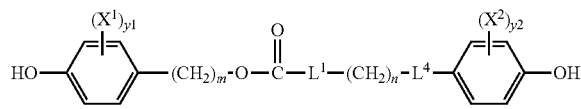

wherein:
y1 and y2 are each independently 0, 1, 2, 3 or 4;
m and n are each independently an integer in the range of 1 to 12;
$X^1$ and $X^2$, at each occurrence, are each independently bromine (Br) or iodine (I);
$L^1$ is selected from the group consisting of a bond, oxygen (—O—); and
$L^4$ is selected from the group consisting of a bond, oxygen (—O—), and optionally substituted phenoxy of formula —$C_6H_4$—O—;
wherein n is not 2; and
wherein when both $L^1$ and $L^4$=bond, then at least one of y1 or y2 is non-zero.

2. The diphenol compound of claim 1, wherein the sum of y1 and y2 is at least 1.

3. The diphenol compound of claim 1, wherein y1 is 1, 2, 3 or 4.

4. The diphenol compound of claim 1, wherein y2 is 1, 2, 3 or 4.

5. The diphenol compound of claim 1, wherein m is 1 or 2; and wherein y1 and y2 are each independently 0, 1 or 2.

6. The diphenol compound of claim 1, wherein m is 2; and wherein y1 and y2 are each independently 0, 1 or 2.

7. The diphenol compound of claim 1, wherein $L^4$ is a bond.

8. The diphenol compound of claim 1, wherein $L^1$ is a bond.

9. The diphenol compound of claim 8, wherein $X^1$=I, y1=2, and y2=0.

10. The diphenol compound of claim 1, wherein $L^1$ is oxygen (—O—).

* * * * *